US010207076B2

(12) United States Patent
Foley et al.

(10) Patent No.: US 10,207,076 B2
(45) Date of Patent: Feb. 19, 2019

(54) INTERMITTENT CATHETERS HAVING HYDRATION/GRIPPER DEVICES

(71) Applicant: Hollister Incorporated, Libertyville, IL (US)

(72) Inventors: Adam J. Foley, Swords (IE); Martin McMenamin, Lifford (IE); Padraig M. O'Flynn, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 241 days.

(21) Appl. No.: 15/111,887

(22) PCT Filed: Mar. 2, 2015

(86) PCT No.: PCT/US2015/018300
§ 371 (c)(1),
(2) Date: Jul. 15, 2016

(87) PCT Pub. No.: WO2015/142506
PCT Pub. Date: Sep. 24, 2015

(65) Prior Publication Data
US 2016/0339205 A1 Nov. 24, 2016

Related U.S. Application Data

(60) Provisional application No. 61/954,095, filed on Mar. 17, 2014.

(51) Int. Cl.
*A61M 25/00* (2006.01)
*A61M 25/01* (2006.01)
*A61M 27/00* (2006.01)

(52) U.S. Cl.
CPC ...... *A61M 25/0045* (2013.01); *A61M 25/002* (2013.01); *A61M 25/0043* (2013.01);
(Continued)

(58) Field of Classification Search
CPC .. A61M 2025/0046; A61M 2025/0062; A61M 2202/0496; A61M 2205/0222;
(Continued)

(56) References Cited

U.S. PATENT DOCUMENTS 3,154,080 A 10/1964 Rowan et al.
4,230,115 A * 10/1980 Walz, Jr. .................. A61F 5/44
604/517

(Continued)

FOREIGN PATENT DOCUMENTS

EP 0677299 4/1995
JP 2001 130634 A 11/1999
(Continued)

OTHER PUBLICATIONS

Hudson and Murahata, "The no-touch method of intermittent urinary catheter insertion: can it reduce the risk of bacteria entering the bladder?", Spinal Cord (2005) 43, 611-614.
(Continued)

*Primary Examiner* — Adam Marcetich
(74) *Attorney, Agent, or Firm* — Cook Alex Ltd.

(57) ABSTRACT

An intermittent catheter has a catheter shaft extending between a proximal end portion and a distal end portion, with a drainage funnel associated with the distal end portion of the catheter shaft. A hydration device encircles at least a portion of the drainage funnel and defines a hydrating fluid-containing reservoir in fluid communication with at least one fluid-release port. The hydration device is configured to be manipulated by a user to move the at least one fluid-release port from a closed condition to an open condition to flow at least a portion of the hydrating fluid out of the reservoir via the at least one fluid-release port for covering at least a portion of the catheter shaft. After or while applying hydrating fluid to the catheter shaft, the
(Continued)

hydration device may be dissociated from the drainage funnel for handling the intermittent catheter.

20 Claims, 15 Drawing Sheets

(52) U.S. Cl.
CPC ..... *A61M 25/0068* (2013.01); *A61M 25/0111* (2013.01); *A61M 27/00* (2013.01); *A61M 25/0017* (2013.01); *A61M 2025/0046* (2013.01); *A61M 2025/0062* (2013.01); *A61M 2202/0496* (2013.01); *A61M 2205/0222* (2013.01); *A61M 2209/06* (2013.01)

(58) Field of Classification Search
CPC .......... A61M 2209/06; A61M 25/0017; A61M 25/002; A61M 25/0043; A61M 25/0045; A61M 25/0068; A61M 25/0111; A61M 27/00; A61M 25/013; A61M 25/0113; A61M 2025/09116; B65D 90/56; F16K 15/147
See application file for complete search history.

(56) References Cited

U.S. PATENT DOCUMENTS

| | | |
|---|---|---|
| 4,652,259 A | 3/1987 | O'Neil |
| 4,834,711 A | 5/1989 | Greenfield et al. |
| 5,242,428 A | 9/1993 | Palestrant |
| 5,454,798 A * | 10/1995 | Kubalak ................... A61F 5/44 600/574 |
| 6,053,905 A * | 4/2000 | Daignault, Jr. .... A61M 25/0111 206/364 |
| 6,409,717 B1 | 6/2002 | Israelsson et al. |
| 6,554,808 B1 * | 4/2003 | Cook .............. A61M 25/09041 604/265 |
| 6,578,709 B1 | 6/2003 | Kavanagh et al. |
| 6,602,244 B2 | 8/2003 | Kavanagh et al. |
| 6,634,498 B2 | 10/2003 | Kayerod |
| 7,476,223 B2 | 1/2009 | McBride |
| 7,601,158 B2 | 10/2009 | House |
| 7,963,908 B2 | 6/2011 | Lindberg |
| 8,181,778 B1 * | 5/2012 | van Groningen ... A61M 25/002 206/364 |
| 8,328,792 B2 | 12/2012 | Nishtala et al. |
| 2001/0001443 A1 | 5/2001 | Kayerod et al. |
| 2002/0103460 A1 * | 8/2002 | Kubalak ............... A61F 5/4404 604/171 |
| 2003/0009079 A1 * | 1/2003 | Beaufore ............... A61F 2/0013 600/29 |
| 2005/0043715 A1 | 2/2005 | Nestenborg et al. |
| 2006/0163097 A1 * | 7/2006 | Murray ............ A61M 25/0009 206/364 |
| 2008/0051630 A1 | 2/2008 | Levey et al. |
| 2008/0097463 A1 * | 4/2008 | House ............... A61M 25/0017 606/108 |
| 2009/0099532 A1 | 4/2009 | Cuevas et al. |
| 2010/0258568 A1 | 10/2010 | Frederiksen et al. |
| 2011/0230864 A1 * | 9/2011 | House ............... A61M 25/0017 604/544 |
| 2012/0168324 A1 | 6/2012 | Carleo |
| 2014/0066905 A1 * | 3/2014 | Young ................ A61M 25/0113 604/544 |
| 2015/0141966 A1 | 5/2015 | Gustavsson |

FOREIGN PATENT DOCUMENTS

| | | |
|---|---|---|
| WO | WO 03/008029 A2 | 1/2003 |
| WO | WO2006/121508 A2 | 11/2006 |
| WO | WO2011/011023 A1 | 1/2011 |

OTHER PUBLICATIONS

Notice of Transmittal of the International Search Report and the Written Opinion of the International Searching Authority for PCT/US2015/018300, dated Aug. 17, 2015.

* cited by examiner

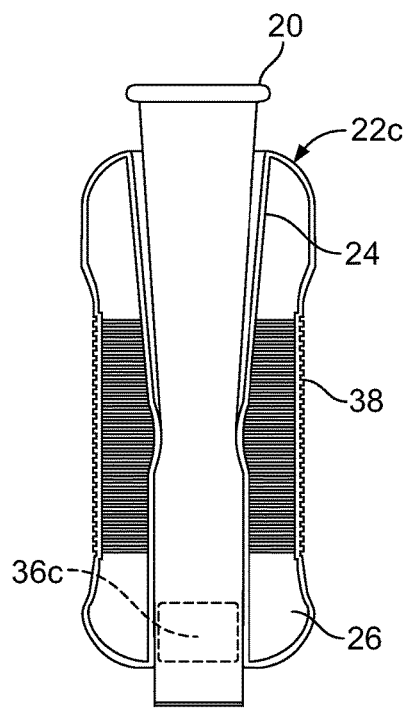
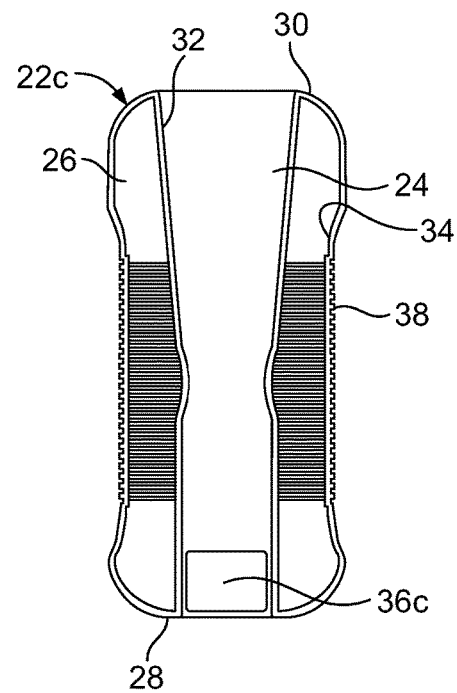
FIG. 12                FIG. 13
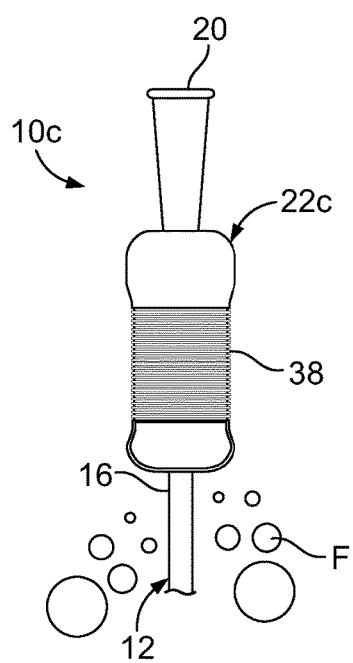
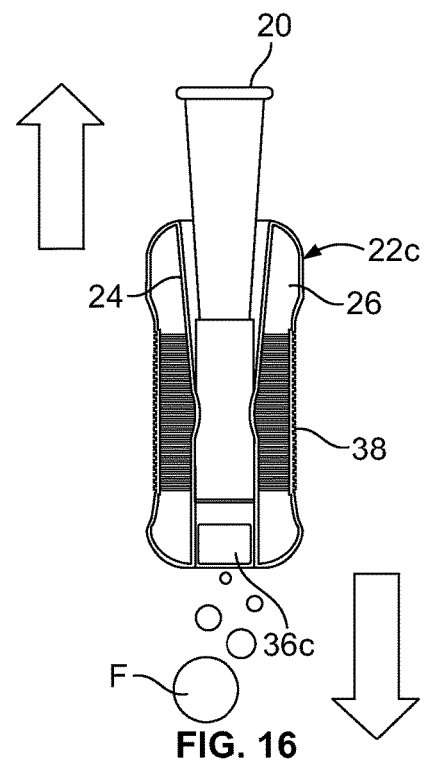
FIG. 15                FIG. 16

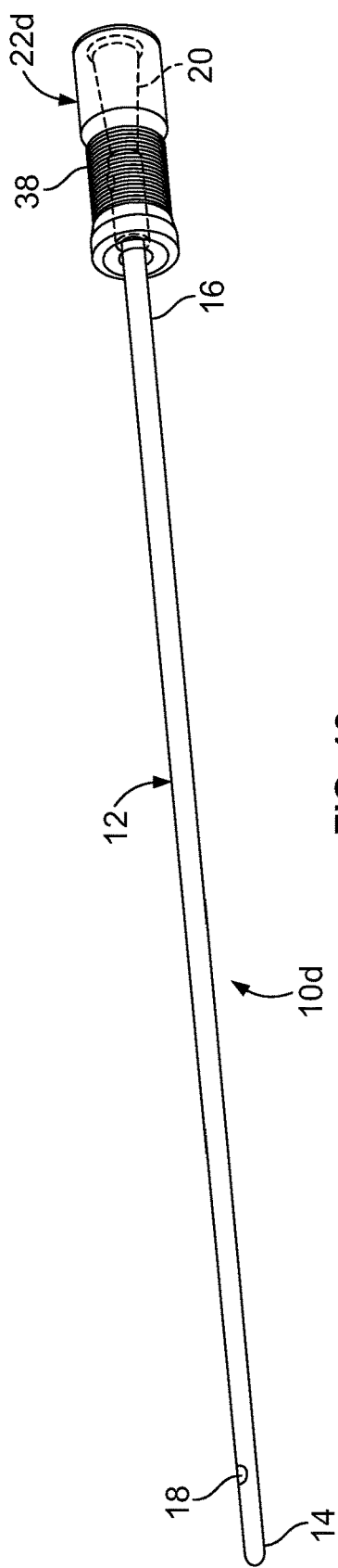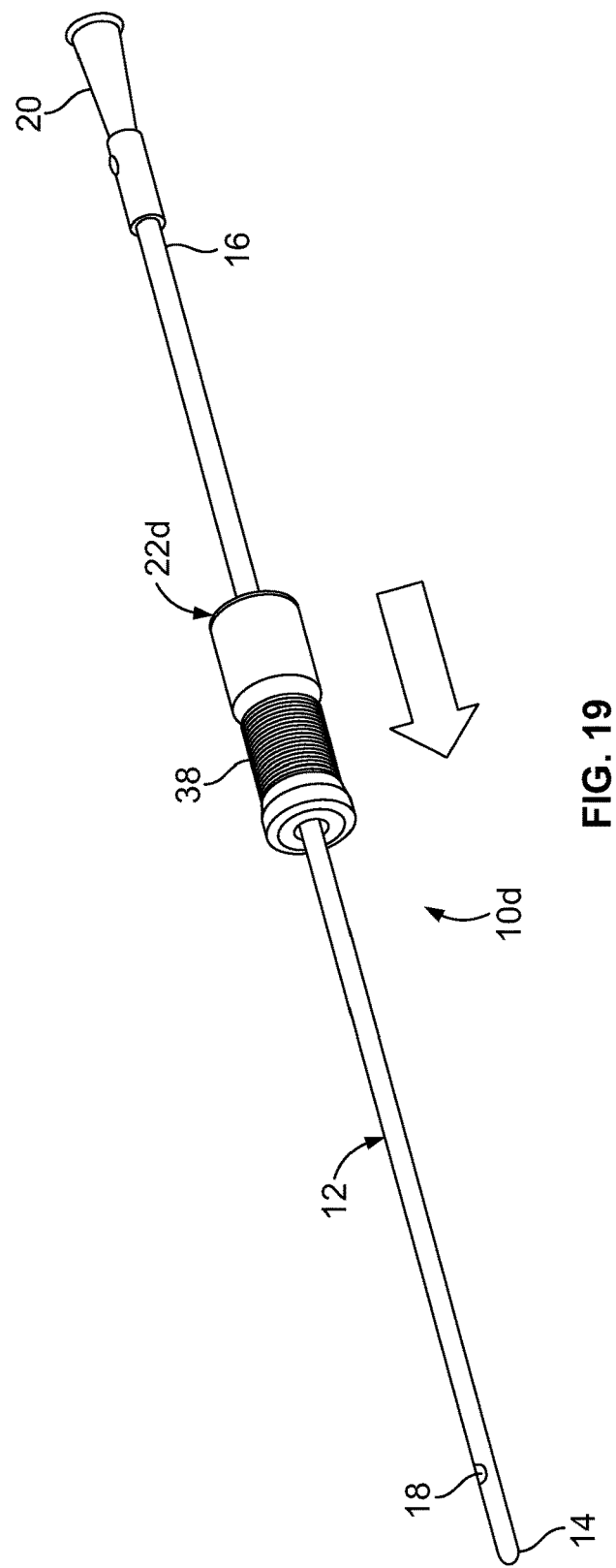

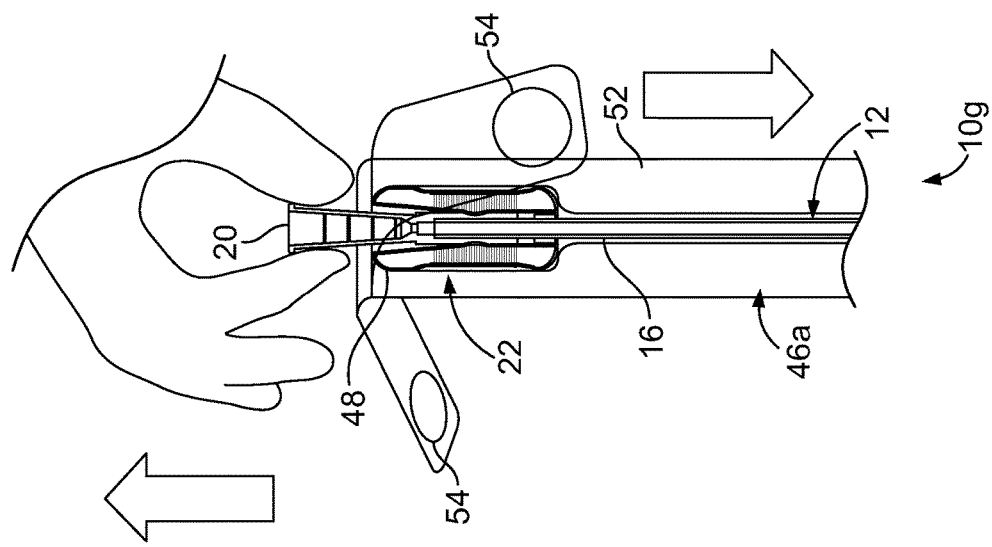
FIG. 26
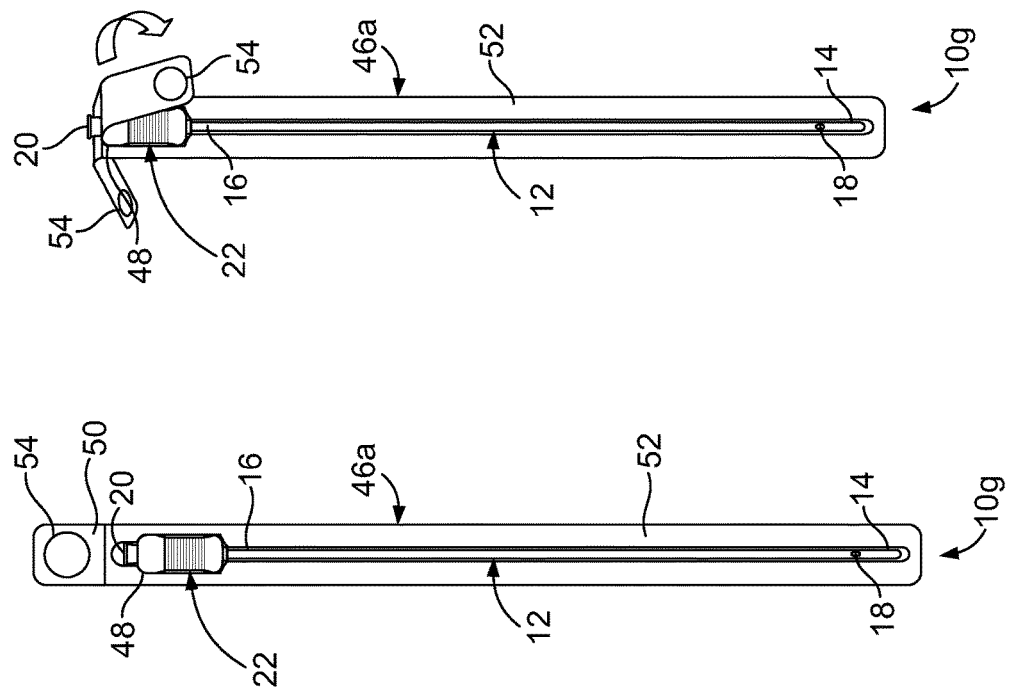
FIG. 25
FIG. 24

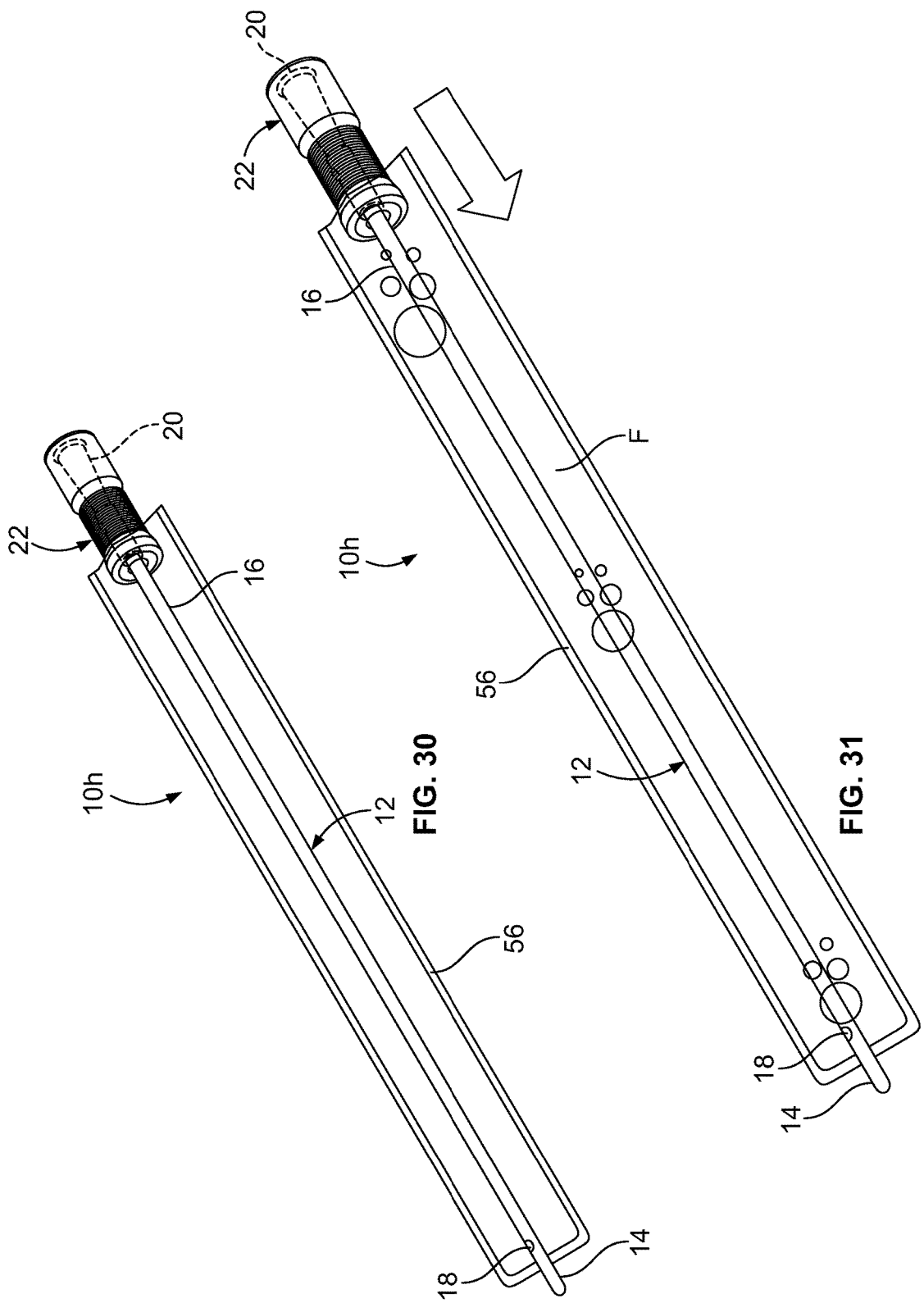

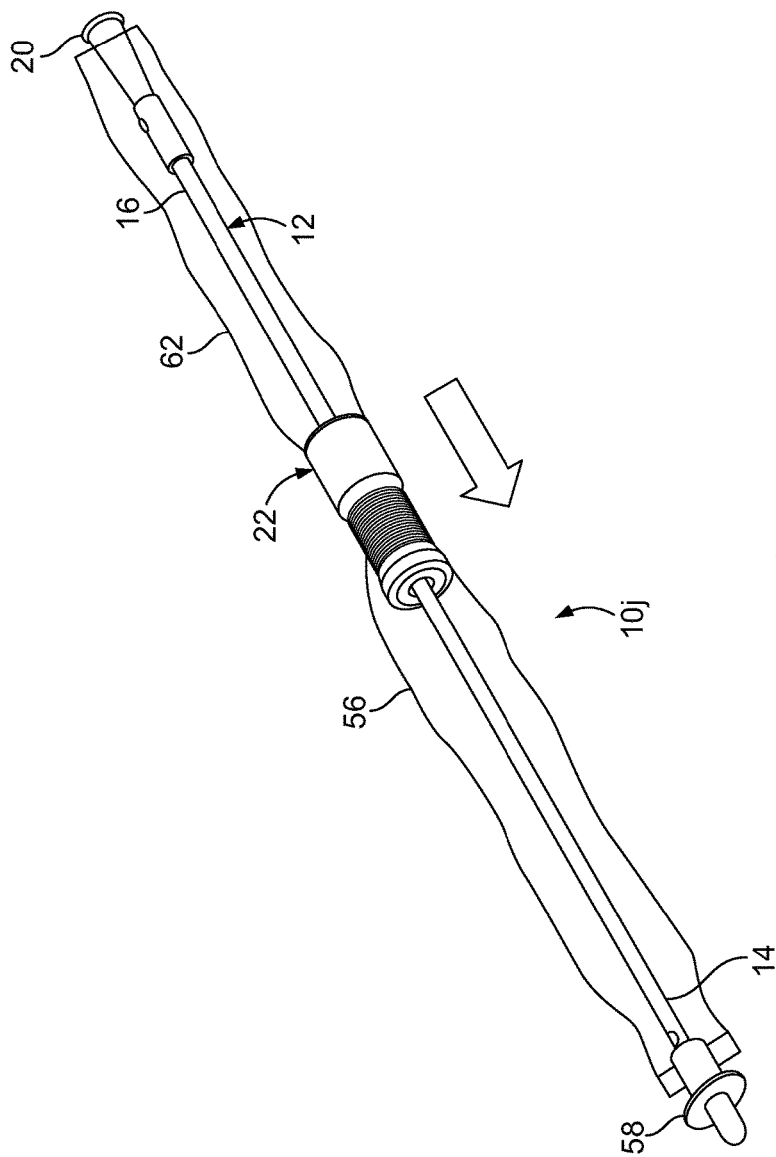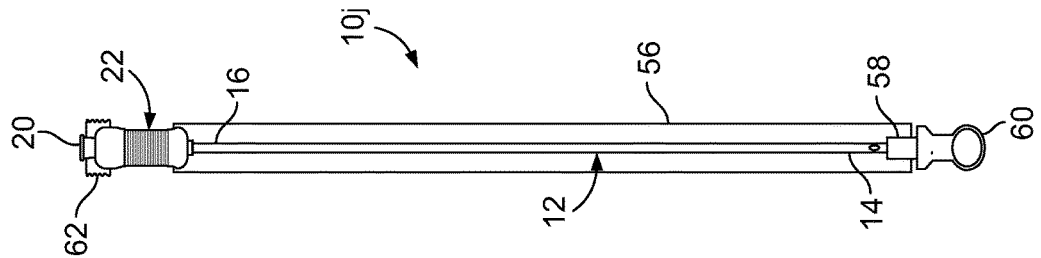

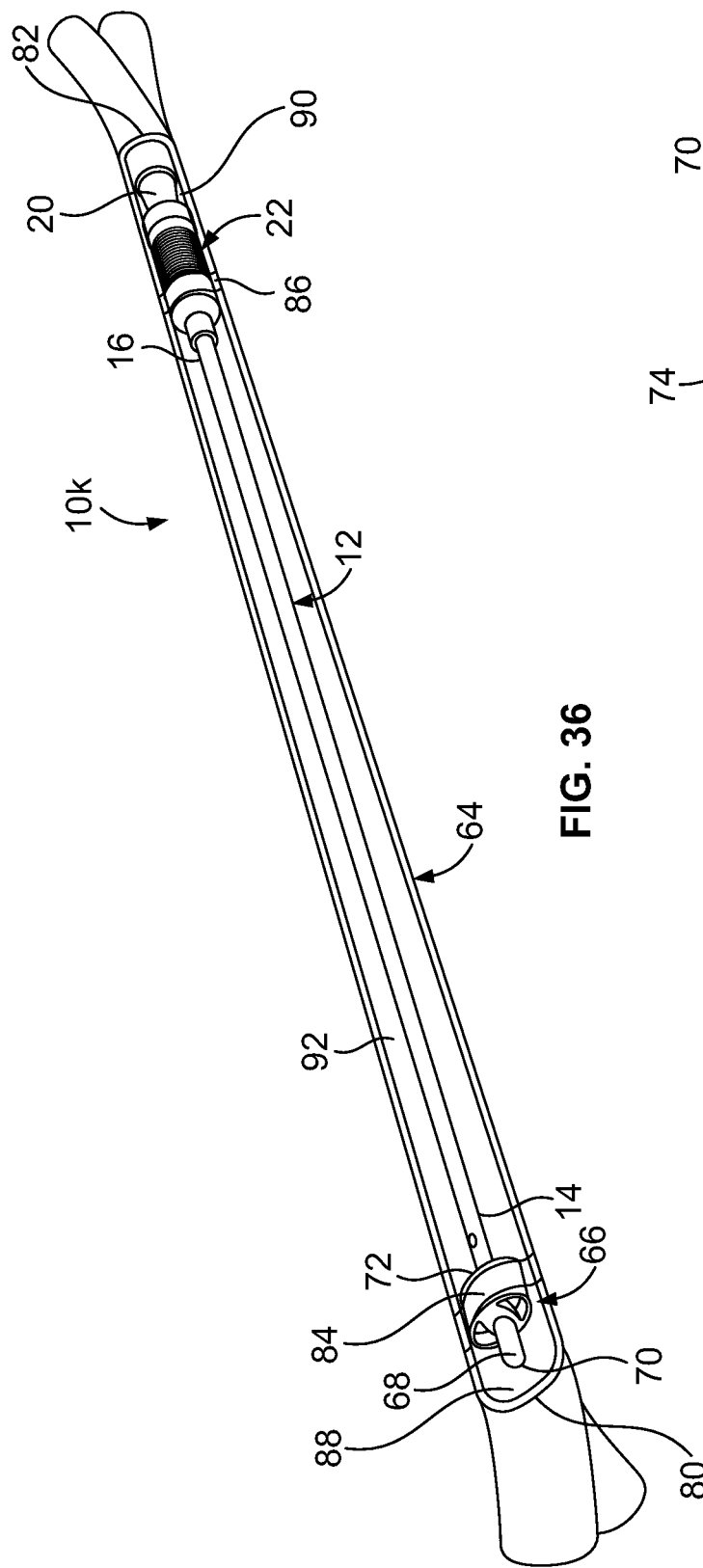
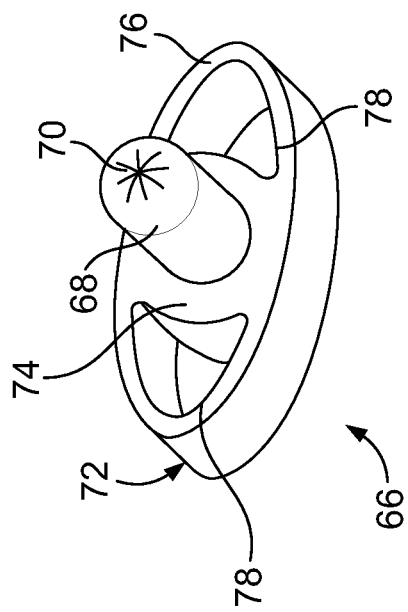
FIG. 36
FIG. 37

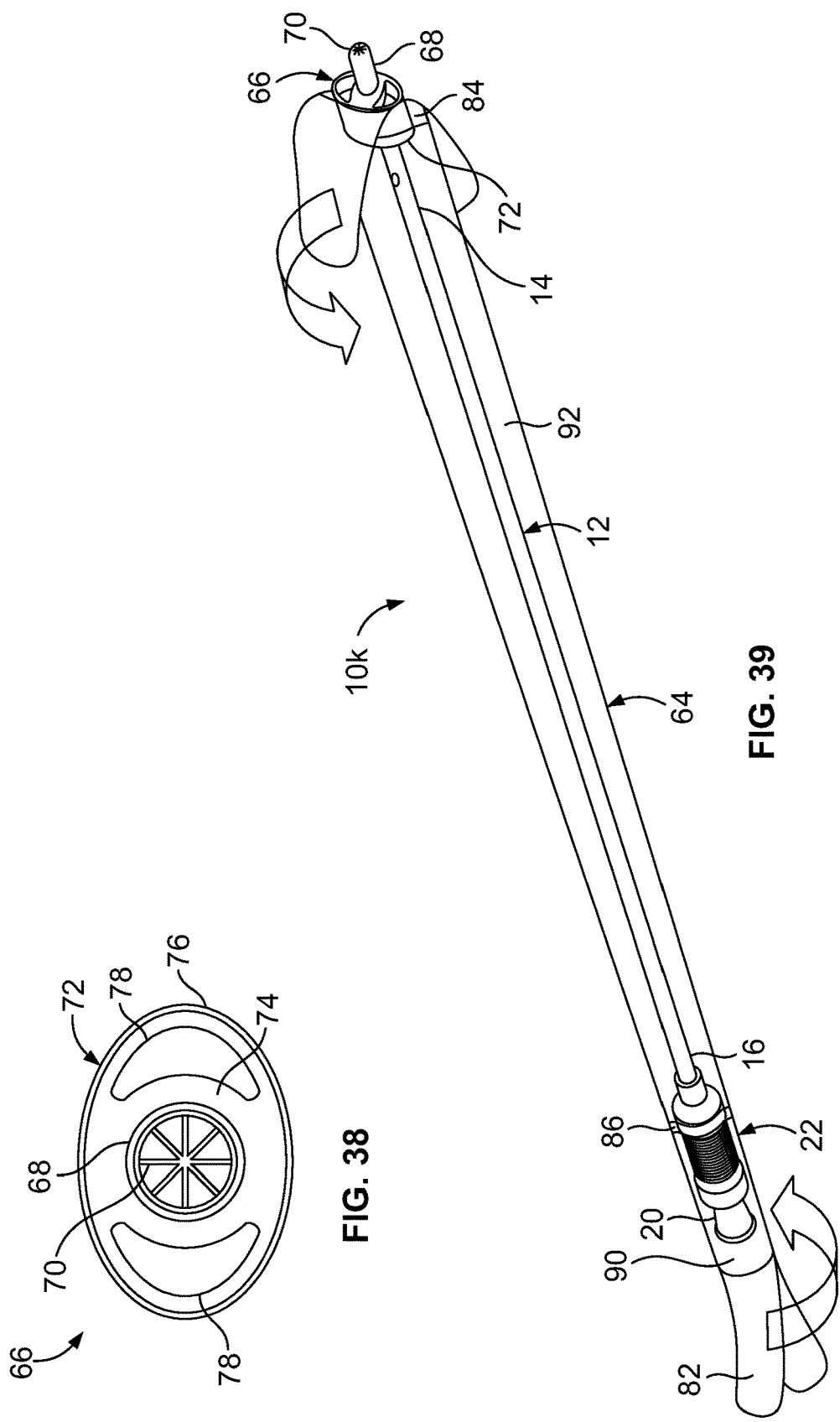

INTERMITTENT CATHETERS HAVING HYDRATION/GRIPPER DEVICES

RELATED APPLICATION

This application is a U.S. national stage application of PCT Patent Application Serial No. PCT/US2015/018300, filed Mar. 2, 2015, which claims the benefit of and priority of U.S. Provisional Patent Application Ser. No. 61/954,095, filed Mar. 17, 2014, the contents of which are incorporated by reference herein.

TECHNICAL FIELD

The present disclosure generally relates to intermittent catheters. More particularly, the present disclosure relates to intermittent catheters having an associated device for hydrating and/or gripping the catheter.

BACKGROUND

Intermittent catheterization is a good option for many users who suffer from various abnormalities and pathologies of the urinary system and its nerve supply. Such catheters are typically provided as single use, individually packaged items and may include a gel-lubricant or hydrophilic coating as a lubricant for reducing friction during insertion into the urethra.

Regarding gel-coated catheters, a user applies a gel-lubricant, such as a water-based gel-lubricant, to the surface of the shaft of the catheter, which reduces friction for ease of insertion into the urethra. In some instances, the gel-lubricant is supplied with the packaged catheter, in which case the gel-lubricant may be applied to the catheter shaft just before or during the packaging operation or as the catheter shaft is being inserted by the user.

When a hydrophilic material is used as a lubricant, a thin coating of hydrophilic material is applied to the outer surface of the catheter shaft, and may subsequently be radiation- or heat-cured. When this coating is activated by swelling in contact with a hydrating liquid or wetting agent such as water, it provides a hydrated surface having an extremely low coefficient of friction. One form of this product provides a sterile, individually packaged, single-use catheter in a dry state or condition. The user opens the package, pours water into the package, waits 30 seconds, and then removes the catheter from the package, which is now ready for insertion. Other embodiments provide the amount of wetting agent necessary for immersion of the catheter shaft in a separate compartment of the package. In such embodiments, the user must open the separate compartment of the package to allow the wetting agent to enter the catheter shaft-containing chamber for direct contact with the hydrophilic coated surface. The catheter is then removed from the package and the catheter shaft is inserted into the urethra. In yet another embodiment, the ready-to-use catheter is provided in a package that already contains enough loose wetting agent to cause it to be immersed. In such an embodiment, the user simply opens the package and removes the catheter therefrom, and then inserts the catheter shaft into the urethra, without the need to add the wetting agent.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, an intermittent catheter includes a catheter shaft extending between a proximal end portion and a distal end portion, with a drainage member associated with the distal end portion of the catheter shaft. A hydration device encircles at least a portion of the drainage member and defines a hydrating fluid-containing reservoir in fluid communication with at least one fluid-release port. The hydration device is configured to be manipulated by a user to move the at least one fluid-release port from a closed condition to an open condition to flow at least a portion of the hydrating fluid out of the reservoir via the at least one fluid-release port for covering at least a portion of the catheter shaft.

In another aspect, an intermittent catheter includes a catheter shaft extending between a proximal end portion and a distal end portion, with an introducer tip associated with the proximal end portion of the catheter shaft. The introducer tip has proximal and distal sections, with the distal section having a barrel portion and a rim portion surrounding the barrel portion. The rim portion is in contact with the barrel portion in at least one location and spaced away from the barrel portion in at least one location to define at least one opening between the barrel and rim portions.

In yet another aspect, a method is provided for hydrating an intermittent catheter. The method involves providing an intermittent catheter including a catheter shaft extending between a proximal end portion and a distal end portion. A drainage member is associated with the distal end portion of the catheter shaft, and a hydration device encircles at least a portion of the drainage member. The hydration device defines a hydrating fluid-containing reservoir in fluid communication with at least one fluid-release port. The hydration device is manipulated to move the at least one fluid-release port from a closed condition to an open condition to flow at least a portion of the hydrating fluid out of the reservoir via the at least one fluid-release port, thereby covering at least a portion of the catheter shaft with the hydrating fluid.

In another aspect, a method is provided for hydrating an intermittent catheter. The method involves providing an intermittent catheter including a catheter shaft extending between a proximal end portion and a distal end portion, with an introducer tip associated with the proximal end portion. A hydrating fluid is applied to the catheter shaft and the introducer tip, with the hydrating fluid first being applied to a portion of the catheter shaft positioned distally of the introducer tip. The hydrating fluid then flows proximally along the catheter shaft to contact a distal section of the introducer tip. The hydrating fluid next flows proximally through at least one opening defined by the distal section of the introducer tip to contact a proximal section of the introducer tip.

BRIEF DESCRIPTION OF THE DRAWINGS

FIG. 12 is a cross-sectional view of the intermittent catheter of FIG. 10;

FIG. 13 is a cross-sectional view of the hydration device of FIG. 10;

FIG. 15 is a front elevational view of the intermittent catheter of FIG. 10, with the hydration device separated from the drainage funnel to release hydrating fluid from the hydration device;

FIGS. 16 and 17 are cross-sectional view of the intermittent catheter of FIG. 10, with the hydration device separated from the drainage funnel to release hydrating fluid from the hydration device;

FIGS. 18 and 19 are perspective views of an intermittent catheter having a hydration device, with the hydration device being used as a gripper device;

FIG. 24 is a side elevational view of an alternative embodiment of an intermittent catheter incorporating a package;

FIG. 25 is a side elevational view of the intermittent catheter of FIG. 24, with a distal portion of the package being opened to access a drainage funnel and hydration device of the catheter;

FIGS. 26 and 27 are side elevational views of the intermittent catheter of FIG. 24, with the hydration device being manipulated to release hydrating fluid therefrom into the package to contact a catheter shaft of the catheter;

FIG. 30 is a perspective view of an embodiment of an intermittent catheter having a hydration device and a sleeve;

FIG. 31 is a perspective view of the intermittent catheter of FIG. 30, with the hydration device having been manipulated to release hydrating fluid into the sleeve;

FIG. 34 is a perspective view of an embodiment of an intermittent catheter having a pair of sleeves secured to a hydration device, with the hydration device in an initial position;

FIG. 35 is a perspective view of the intermittent catheter of FIG. 34, with the hydration device moved proximally along a catheter shaft of the catheter;

FIG. 36 is a perspective view of an embodiment of an intermittent catheter positioned within a sleeve package;

FIG. 37 is a perspective view of an introducer tip of the intermittent catheter of FIG. 36;

FIG. 38 is a top plan view of the introducer tip of the intermittent catheter of FIG. 38; and FIG. 39 is a perspective view of the intermittent catheter of FIG. 36, with a sealed proximal chamber and a sealed distal chamber of the sleeve package being opened for use of the catheter.

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figures 1, 2:
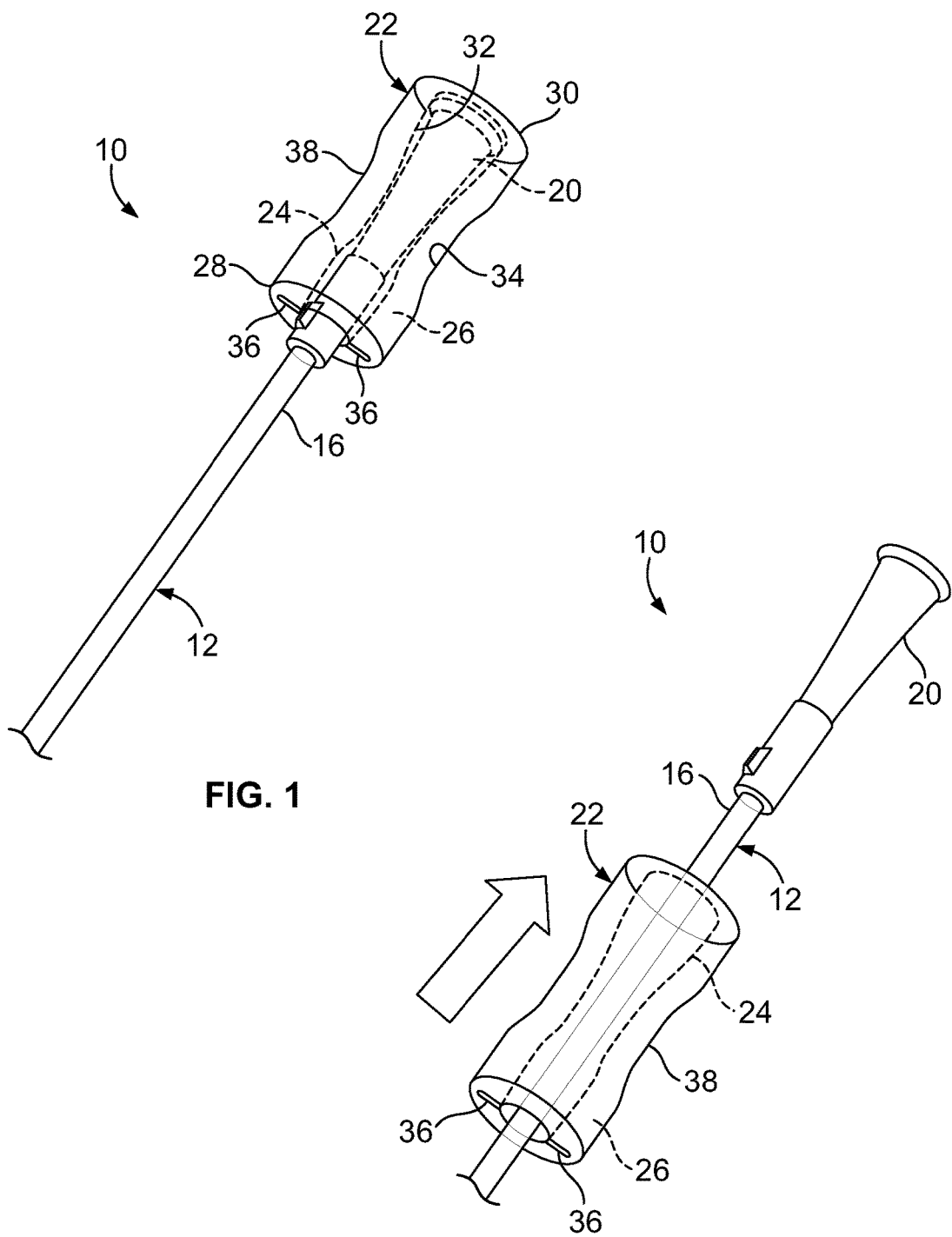
FIG. 1 is a perspective view of an intermittent catheter having a hydration device according to an aspect of the present disclosure.
FIG. 2 is a perspective view of the intermittent catheter of FIG. 1, showing the hydration device being secured to a drainage funnel of the catheter.
Figure 3:
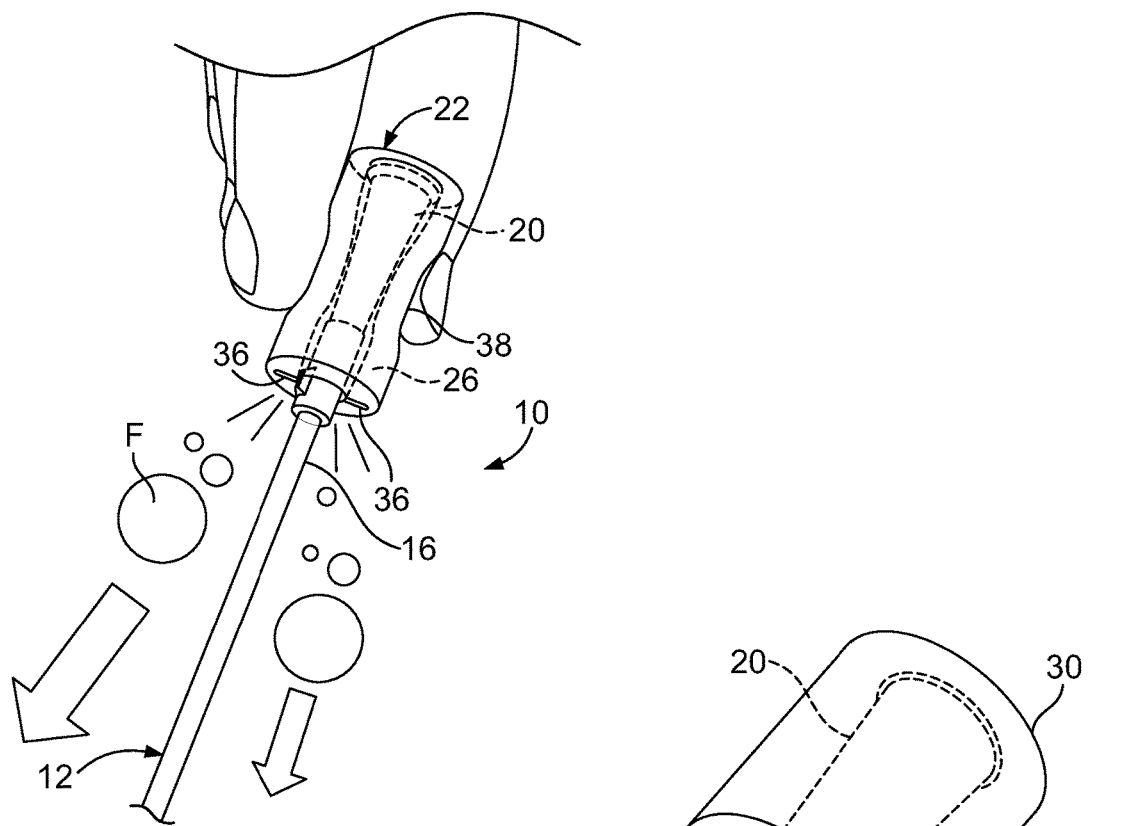
FIG. 3 is a perspective view of the intermittent catheter of FIG. 1, with the hydration device being manipulated to release a hydrating fluid.
Figure 4:
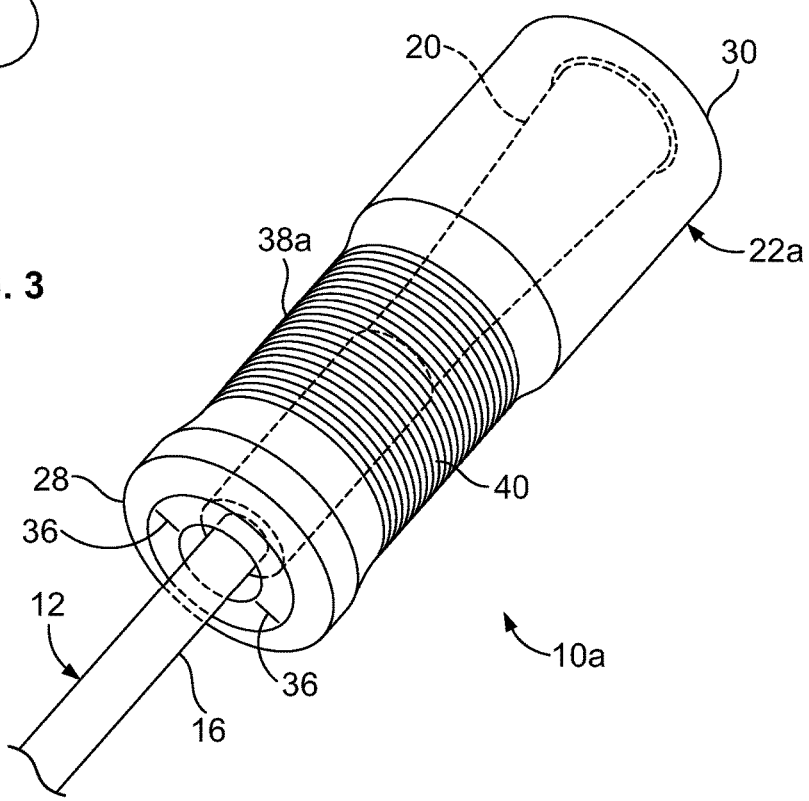
FIG. 4 is a perspective view of an alternative embodiment of an intermittent catheter having a hydration device.
Figure 5:
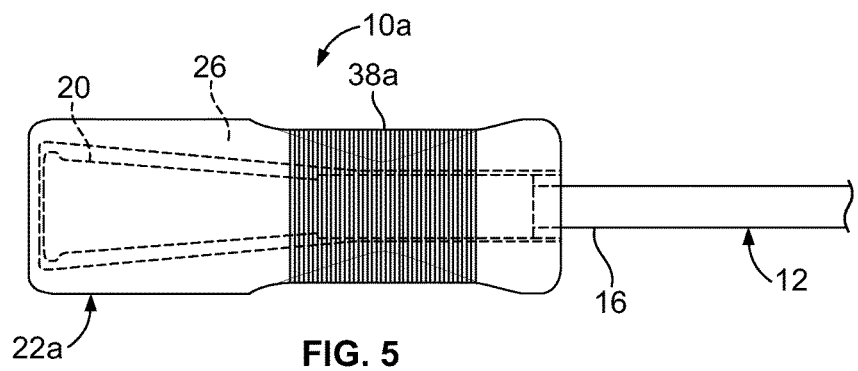
FIG. 5 is a side elevational view of the intermittent catheter of FIG. 4.

FIGS. 1-3 show a distal portion of an intermittent catheter 10 according to an aspect of the present disclosure. The intermittent catheter 10 will be described herein in terms of its applicability for catheterization of a male urethra, but it should be understood that catheters according to the present disclosure may be used for other applications as well.

The illustrated intermittent catheter 10 includes a generally flexible catheter shaft 12, which extends between a closed proximal end portion 14 (FIG. 18) and an open distal end portion 16. The catheter shaft 12 may be provided generally according to conventional design, such as with one or more openings or eyes 18 associated with the proximal end portion 14 for flowing a fluid from the outside environment into the hollow interior of the catheter shaft 12. The distal end portion 16 is illustrated with an associated drainage member, such as a funnel 20, which may be a generally rigid component that is secured to the distal end portion 16 of the catheter shaft 12. The drainage funnel 20 may be configured to direct fluid from out of the interior of the catheter shaft 12 to a collection container or disposal device, such as a toilet. The catheter shaft 12 may be provided as a hydrophilic catheter shaft, in which case it may include a hydrophilic outer surface along at least a portion of its length. If provided, the hydrophilic portion of the catheter shaft becomes lubricious when wetted or hydrated with a hydration fluid, such as water or saline. All or a portion of the catheter shaft itself may have hydrophilic properties or, alternatively, a coating may be applied to at least a portion of the outer surface of the catheter shaft to give the coated portion hydrophilic properties.

The intermittent catheter 10 further includes a hydration device 22. As used herein, the term "hydration device" is intended to refer broadly to a device of the type to be described herein, rather than being limited to particular uses or fluid contents. For example, it should be understood that a "hydration device" may be used for either hydrating or lubricating a portion of a catheter shaft and may contain either a hydrating or lubricating fluid, as will be described below.

The hydration device 22 is associated with and encircles at least a portion of the drainage funnel 20 (FIGS. 1 and 3). FIG. 2 shows a step of the process of assembling the intermittent catheter 10, in which the proximal end portion 14 of the catheter shaft 12 is advanced into a central cavity 24 defined by the generally tubular hydration device 22. The hydration device 22 is advanced distally along the catheter shaft 12 until the drainage funnel 20 is at least partially positioned within the cavity 24, as in FIGS. 1 and 3. Preferably, the cavity 24 of the hydration device 22 is configured to engage and be retained upon the drainage funnel 20, such that the hydration device 22 remains connected to the hydration device 22 after pressing the hydration device 22 distally onto the drainage funnel 20. In one embodiment, the cavity 24 of the hydration device 22 may have a shape that complements the shape of the drainage funnel 20. The hydration device 22 (or at least the portion thereof which defines the cavity 24) may have intermediate rigidity (i.e., greater flexibility than the drainage funnel 20 and greater rigidity than the catheter shaft 12), which may be advantageous to allow the hydration device 22 to temporarily deform and pass over the contours of the drainage funnel 20 as it is pressed onto the drainage funnel 20.

The hydration device 22 includes a reservoir 26, which is defined between proximal and distal ends 28 and 30 and inner and outer walls 32 and 34 of the hydration device 22. The reservoir 26 is at least partially filled with a hydrating fluid F, which is applied to at least a portion of the catheter shaft 12 prior to insertion of the catheter shaft 12 into a body lumen. The nature of the hydrating fluid F may vary without departing from the scope of the present disclosure. For example, in one embodiment, the hydrating fluid comprises water or another wetting fluid, which interacts with hydrophilic material of the catheter shaft 12 to provide a lubricated surface. In other embodiments, a gel or oil or other lubricating fluid may be provided as a hydrating fluid F, and the present disclosure is not limited to a particular hydrating or lubricating fluid. Preferably, the reservoir 26 is at least partially filled with the hydrating fluid F prior to advancing the hydration device 22 onto the drainage funnel 20, but it is also within the scope of the present disclosure for the hydration device 22 to be secured to the drainage funnel 20 prior to adding the hydrating fluid F into the reservoir 26.

The reservoir 26 is provided in fluid communication with at least one fluid-release port or vent or seal 36. In the illustrated embodiment, the proximal end 28 includes a pair of fluid-release ports 36, which are positioned on opposite sides of the cavity 24, but it within the scope of the present disclosure for the hydration device 22 to include only one fluid-release port or more than two fluid-release ports and/or for the fluid-release port(s) to be located at a different position than shown in FIGS. 1-3. The hydration device 22 is resiliently deformable in the vicinity of the fluid-release ports 36, such that the fluid-release ports 36 may be manipulated by a user to move the fluid-release ports 36 between a closed condition (FIGS. 1 and 2) and an open condition (FIG. 3). In the closed condition, the fluid-release ports 36 provide seals, which prevents the release of hydrating fluid F from the reservoir 26. In the open condition, the fluid-release ports 36 are at least partially open to allow for at least a portion of the hydrating fluid F to flow out of the reservoir 26 via the fluid-release ports 36. The fluid-release portions 36 may be sealed by any suitable means such as, but not limited to, friction, a heat seal, or an adhesive.

In use, the intermittent catheter 10 is oriented with the drainage funnel 20 positioned above the catheter shaft 12. The hydration device 22 is then manipulated by a user to move at least one of the fluid-release ports 36 from the closed condition to the open condition to allow at least a portion of the hydrating fluid F to flow out of the reservoir 26 via the fluid-release port(s) 36 to cover at least a portion of the catheter shaft 12. The hydrating fluid F will wet the hydrophilic surface of the catheter shaft 12 (when a hydrophilic catheter shaft or coating is employed) or otherwise lubricate the catheter shaft 12 (when the catheter shaft is formed of a non-hydrophilic material and omits a hydrophilic coating). By positioning the drainage funnel 20 above the catheter shaft 12, the hydrating fluid F will flow from the distal end portion 16 of the catheter shaft 12 down to the proximal end portion 14 via gravity, thereby covering and coating the catheter shaft 12 for increased lubricity.

When the catheter shaft 12 has been lubricated by the application of hydrating fluid F, it may be advanced into a body lumen. In one exemplary procedure, the proximal end portion 14 of the catheter shaft 12 is advanced into and through a urethra until the proximal end portion 14 reaches the bladder. When the proximal end portion 14 is positioned within the bladder, urine contained within the bladder will flow into the interior of the catheter shaft 12 via the eye(s) 18. The urine then flows from the proximal end portion 14 of the catheter shaft 12 to the distal end portion 16, where it exits the intermittent catheter 12 via the drainage funnel 20. Thereafter, the catheter shaft 12 may be retracted from the urethra and the intermittent catheter 10 may be disposed of.

The hydration device 22 may be manipulated in any suitable manner to open the fluid-release port(s) 36. For example, in one embodiment, the outer wall 34 of the hydration device 22 is pinched or squeezed to move it toward the inner wall 32 (FIG. 3), which causes the fluid-release port(s) 36 to resiliently deform from the closed condition to the open condition. When the fluid-release ports 36 are sealed by an adhesive or heat seal or the like, squeezing the hydration device 22 increases the pressure within the reservoir 26 until the pressure overcomes the strength of the seal, which bursts or yields to allow the release of hydrating fluid F. If the hydration device 22 is configured to be manipulated by squeezing or pinching, the outer wall 34 may be textured or contoured for improved handling. For example, in the illustrated embodiment, the outer wall 34 of the hydration device 22 includes a gripping portion 38, which is sufficiently flexible to be moved toward the inner wall 32. The outer surface of the illustrated gripping portion 38 has a smaller diameter than the outer surface of the outer wall 34, which may be sized and configured to receive the digits of a user, as shown in FIG. 3. The outer wall 34 may be thinner at the gripping portion 38 than at other portions or may otherwise be more flexible than other portions of the outer wall 34, with the smaller diameter serving to encourage the user to place his digits onto the gripping portion 38. At least a portion of the outer surface of the gripping portion 38 may be textured or contoured (e.g., with ribs or knurls or the like) for improved handling. The material composition of the hydration device 22 or only the gripping portion 38 thereof may also provide improved handling. For example, the hydration device 22 or only the gripping portion 38 thereof may be formed of a soft elastomeric material, such as silicone, which may be gripped by a user without the digits of the user sliding along the hydration device 22 or gripping portion 38.

FIGS. 4-7 illustrate an intermittent catheter 10a with a variation of the hydration device 22 of FIGS. 1-3. In the embodiment of FIGS. 4-7, the hydration device 22a is similar to the hydration device 22 of FIGS. 1-3, but with a differently configured gripping portion 38a. In the embodiment of FIGS. 1-3, the gripping portion 38a is positioned approximately midway between the proximal and distal ends 28 and 30 of the hydration device 22, whereas the gripping portion 38a of the hydration device 22a of FIGS. 4-7 is positioned closer to the proximal end 28 than the distal end 30. In other embodiments, the gripping portion (if provided) may be positioned closer to the distal end of the hydration device than to the proximal end. Additionally, the gripping portion 38 of FIGS. 1-3 is shown as being generally flat and featureless, while the gripping portion 38a of FIGS. 4-7 is shown with ribs 40 for improved gripping and handling.

Figure 6:
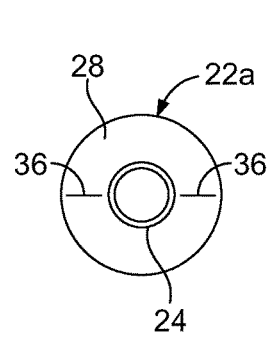
FIG. 6 is an end view of the hydration device of FIG. 4, with fluid-release ports thereof in a closed condition.
Figure 7:
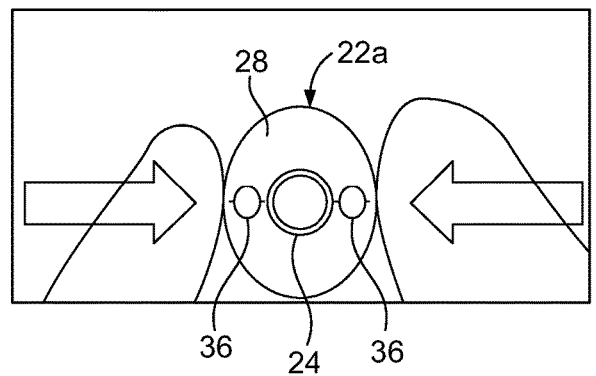
FIG. 7 is an end view of the hydration device of FIG. 4, with fluid-release ports thereof in an open condition.

FIG. 6 is an end view of the hydration device 22a, with the fluid-release ports 36 in a closed condition. FIG. 7 shows the hydration device 22a being manipulated by pinching or squeezing, which causes the fluid-release ports 36 to move from the closed condition to an open condition, as described above. In the illustrated embodiment, the fluid-release ports 36 are configured as radial slits, which are positioned on opposite sides of the cavity 24 of the hydration device 22a in a common line or plane (e.g., along a diameter of the hydration device 22a). When the fluid-release ports 36 are oriented as shown in FIGS. 6 and 7, they may be best opened by squeezing or pinching the hydration device 22a along the same line or in the same plane in which the fluid-release ports 36 lie, as shown in FIG. 7, although they may also be opened by pinching or squeezing the hydration device 22a along a different line or in a different (preferably non-perpendicular) plane. If the hydration device has a preferred line or plane of manipulation, the hydration device or the gripping portion (if provided) may be configured to alert the user to the preferred line or plane of manipulation. For example, the hydration device may have graphics or colors that highlight the preferred line or plane of manipulation or may be non-symmetrical to alert the user to the preferred line or plane of manipulation.

Figure 8:
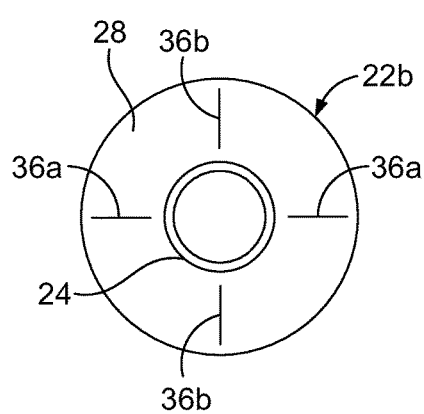
FIG. 8 is an end view of an alternative embodiment of a hydration device, with fluid-release ports thereof in a closed condition.
Figure 9:
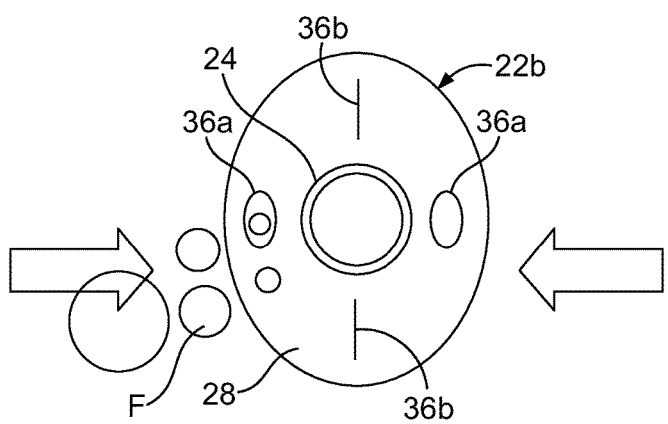
FIG. 9 is an end view of the hydration device of FIG. 8, with fluid-release ports thereof in an open condition.

FIGS. 8 and 9 illustrate an alternative embodiment of a hydration device 22b. In the embodiment of FIGS. 8 and 9, the hydration device 22b includes fluid-release ports 36a and 36b positioned in more than one line or plane. In the illustrated embodiment, there are four fluid-release ports that are symmetrically spaced around the cavity 24 of the hydration device 22b, but it is also within the scope of the present disclosure for there to be a different number of fluid-release ports and for the fluid-release ports to be non-symmetrically arranged around the cavity 24. Each fluid-release port may be in fluid communication with a common reservoir. Alternatively, a hydration device may be provided with a plurality of reservoirs, with each reservoir being in fluid communication with one or more different fluid-release ports.

With fluid-release ports 36a and 36b arranged in different lines or planes, pinching or squeezing or otherwise manipulating the hydration device 22b along one line or plane may cause selected fluid-release ports to open to a different extent than other fluid-release ports. For example, in the orientation of FIGS. 8 and 9, pinching or squeezing or manipulating the hydration device 22b along a horizontal line or in a horizontal plane (as in FIG. 9), the fluid-release ports 36a which lie in that same line or plane will tend to open to a greater extent than the fluid-release ports 36b that are arranged along another line or plane. If the fluid-release ports 36a and 36b are defined as slits oriented perpendicular to the line or plane of manipulation, the fluid-release ports 36b may tend to remain in the closed condition, as shown in FIG. 9. Similarly, if the hydration device 22b is manipulated along a vertical line or plane (in the orientation of FIGS. 8 and 9), the fluid-release ports 36b arranged along that same line or in that same plane will tend to open, whereas the fluid-release ports 36a arranged along the perpendicular line or plane will tend to remain closed.

If the hydration device 22b is manipulated along a line or plane that is different from (and preferably non-perpendicular to) the line or plane in which a fluid-release port 36a, 36b is defined (e.g., in non-vertical, non-horizontal line or plane in the orientation of FIGS. 8 and 9), it may tend to cause that fluid-release port 36a, 36b to open. Accordingly, the hydration device 22b of FIGS. 8 and 9 may be considered to be substantially omni-directional, to the extent that at least one of the fluid-release ports 36a, 36b will be at least partially opened regardless of the line(s) or plane(s) in which the hydration device 22b is manipulated. In certain applications, a more direction-dependent configuration (e.g., the configuration of FIGS. 6 and 7) may be advantageous, whereas an omni-directional configuration (as in the configuration of FIGS. 8 and 9) may be preferred for other applications.

FIGS. 1-9 show hydration devices having fluid-release ports that are spaced away from the central cavity of the hydration device, but it is also within the scope of the present disclosure for at least one of the fluid-release ports to be in fluid communication with the central cavity (i.e., extending between the reservoir and the cavity). For example, FIGS. 10-17 illustrate an intermittent catheter 10c having a hydration device 22c that may be provided generally according to the foregoing description of the hydration devices of FIGS. 1-9, except that at least one fluid-release port 36c is in fluid communication with the cavity 24 defined inwardly of the inner wall 32 of the hydration device 22c.

The fluid-release ports 36c may be configured to move between closed and open conditions by either deformation of the fluid-release ports 36c or by movement of the hydration device 22c with respect to the drainage funnel 20. If the fluid-release ports 36c are configured to be deformed, then they may be provided as slits (as in the embodiments of FIGS. 1-9), with the hydration device 22c being pinched or squeezed or otherwise manipulated as described above to move the fluid-release ports 36c between open and closed conditions. When the fluid-release ports 36c have been moved into the open condition, hydrating fluid F flows out of the reservoir 26, through the fluid-release ports 36c, and into the cavity 24, where it contacts the drainage funnel 20 and/or the catheter shaft 12 for lubrication prior to advancement of the catheter shaft 12 into a body lumen.

Figure 10:
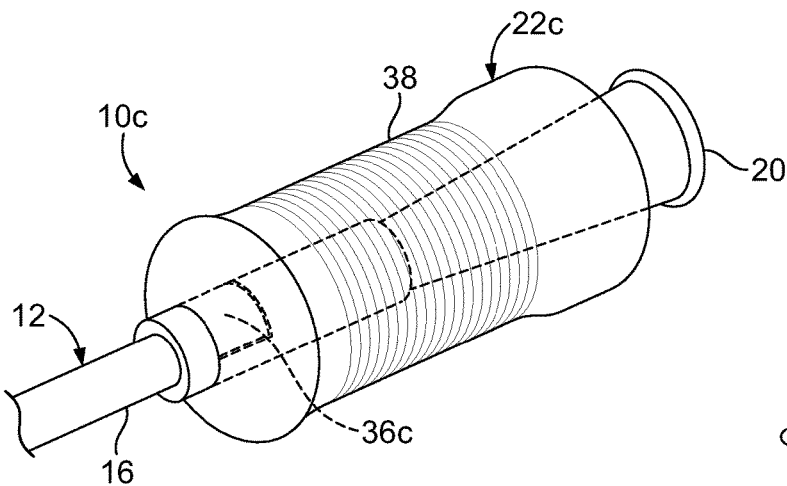
FIG. 10 is a perspective view of another alternative embodiment of an intermittent catheter having a hydration device.
Figure 11:
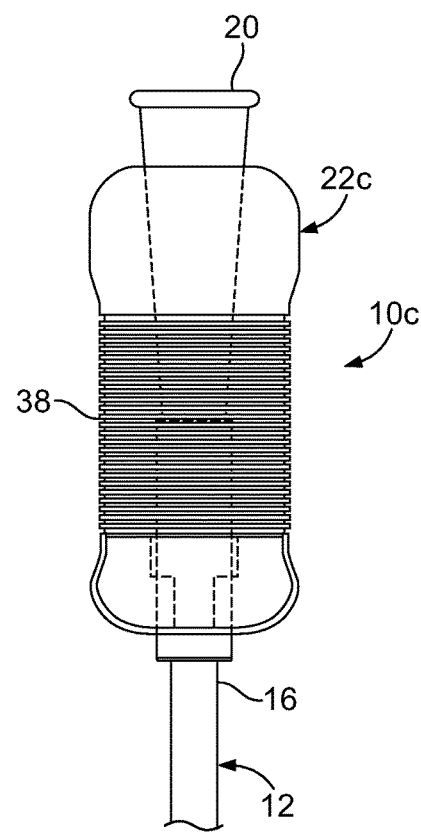
FIG. 11 is a side elevational view of the intermittent catheter of FIG. 10.
Figure 14:
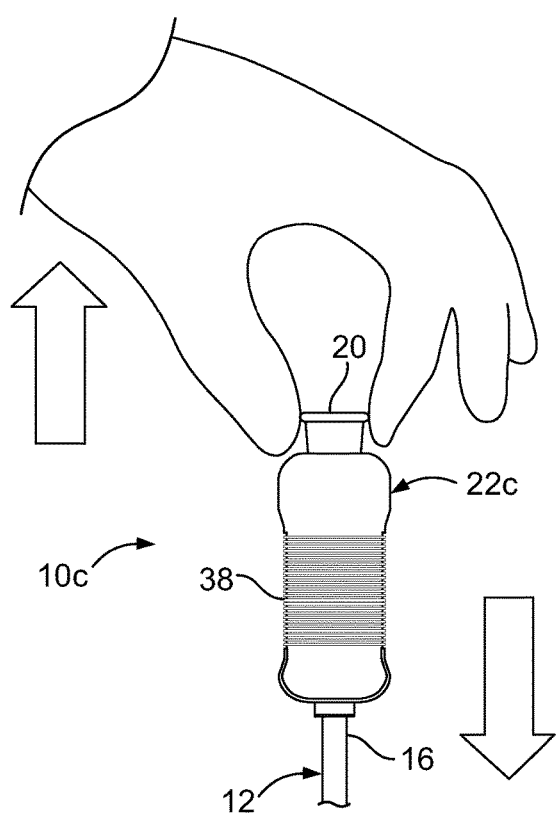
FIG. 14 is a side elevational view of the intermittent catheter of FIG. 10, with the hydration device being separated from a drainage funnel to release hydrating fluid from the hydration device.

If the fluid-release ports 36c are configured to be moved into an open condition by movement of the hydration device 22c with respect to the drainage funnel 20, the fluid-release ports 36c may be defined by open passages (FIG. 13) rather than slits. Fluid flow through the fluid-release ports 36c may be initially prevented by a portion of the drainage funnel 20 overlaying or plugging the fluid-release ports 36c (FIGS. 10-12). The fluid-release ports 36c may be moved from this closed condition to an open condition by moving the hydration device 22c proximally along the catheter shaft 12, away from the drainage funnel 20 (FIGS. 14-17). So moving the hydration device 22c removes the blockage from the fluid-release ports 36c, thereby allowing hydrating fluid F to flow out of the reservoir 26, through the fluid-release ports 36c, and into contact with the catheter shaft 12 for lubrication. If this mechanism is selected for opening the fluid-release ports 36c, the hydration device 22c may be formed of a more rigid material than what may be preferred when the fluid-release ports are opened by pinching or squeezing. However, it may be advantageous for at least the inner wall 32 of the hydration device 22c to be semi-flexible to allow the hydration device 22c to be pressed onto the drainage funnel 20 for an interference fit and later separated from the drainage funnel 20 to release hydrating fluid F.

After releasing hydrating fluid (or while releasing hydrating fluid), the hydrating device may be used as a gripper device for handling the intermittent catheter. For example, FIG. 18 shows a hydration device 22d secured to the drainage funnel 20 of an intermittent catheter 10d. If the hydration device 22d is configured to release hydrating fluid by pinching or squeezing or the like, then it may be moved proximally along the catheter shaft 12 (FIG. 19) after being manipulated. Alternatively, the hydration device 22d may be moved proximally along the catheter shaft 12 prior to or while manipulating the hydration device 22d to release hydrating fluid. If the hydration device 22d is configured to be moved proximally along the catheter shaft 12, then it may continue releasing hydrating fluid as it is moved away from the drainage funnel 20 and along the catheter shaft 12.

With the hydration device 22d encircling the catheter shaft 12, it may be pinched or squeezed to move the outer wall 34 into engagement with the inner wall 32, which may then be further pressed inwardly to engage the catheter shaft 12. This causes the hydration device 22d to grip the catheter shaft 12, thereby allowing the user to handle and manipulate the catheter shaft 12 (including advancing the proximal end portion 14 of the catheter shaft 12 into a body lumen) by holding the hydration device 22d rather than the lubricated catheter shaft 12.

Figure 20:
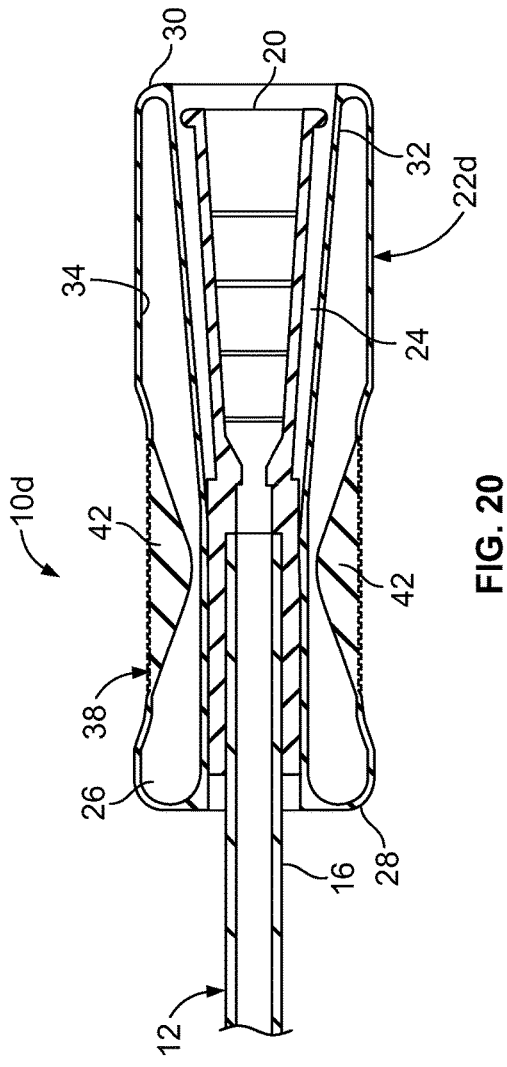
FIG. 20 is a cross-sectional view of the hydration device of FIG. 18.

The hydration device 22d may include one or more features or formations for improved functionality as a gripper device. For example, FIG. 20 shows the outer wall 34 of the hydration device 22d having an extension or gripping aid 42, which may be associated with the gripping portion 38 (if provided). The extension 42 is positioned on an inner surface of the outer wall 34, within the reservoir 26, and extends toward the inner wall 32, preferably without contacting the inner wall 32. When the outer wall 34 is pressed toward the inner wall 32, the extension 42 is brought into contact with the outer surface of the inner wall 32. Compared to a hydration device omitting an extension, the extension 42 effectively positions the outer wall 34 closer to the inner wall 32, thereby allowing for a smaller deformation of the outer wall 34 to effectively place the outer wall 34 into contact with the inner wall 32.

Figure 21:
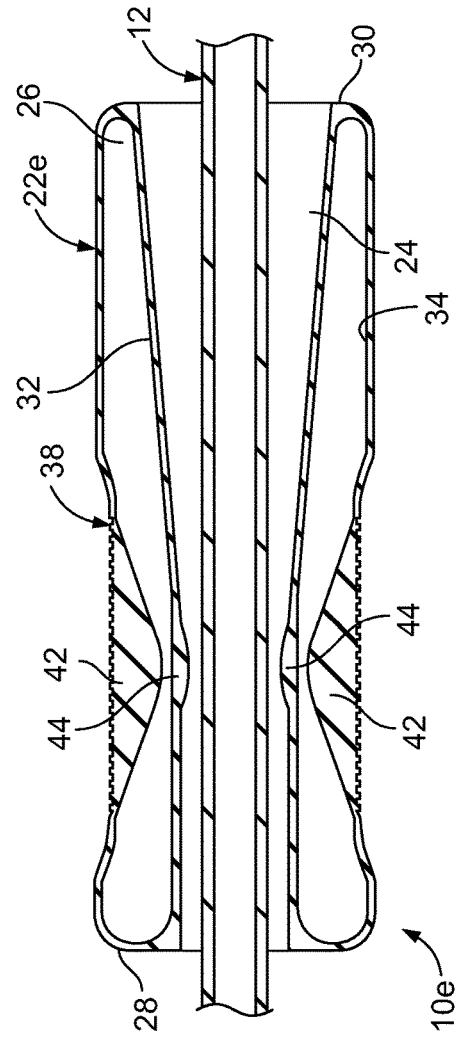
FIG. 21 is a cross-sectional view of an alternative embodiment of a hydration device which may be used as a gripper device.
Figure 17:
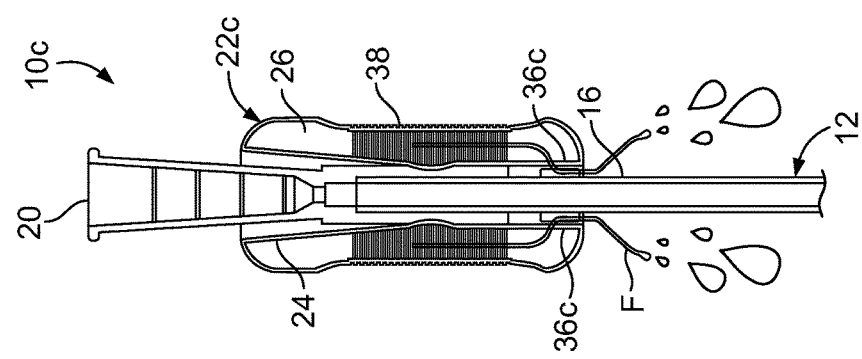

FIG. 21 shows an embodiment in which both the outer and inner walls 34 and 32 of the hydration device 22e of the intermittent catheter 10e include radially inwardly extending extensions or gripping aids 42 and 44. The extension 44 of the inner wall 32 is positioned on an inner surface of the inner wall 32, within the central cavity 24 of the hydration device 22e. Preferably, the extension 44 of the inner wall 32 is generally aligned with the gripping portion 38 and/or the extension 42 of the outer wall 34, if provided. When the inner wall 32 is pressed toward the catheter shaft 12, the extension 44 is brought into contact with the catheter shaft 12. Compared to a hydration device omitting such an extension, the extension 44 effectively positions the inner wall 32 closer to the catheter shaft 12, thereby allowing for a smaller deformation of the inner wall 32 to effectively place the inner wall 32 into contact with the catheter shaft 12. Providing both extensions 42 and 44 may be advantageous by decreasing the force required to grip the catheter shaft 12 with the hydration device 22e, but it is also within the scope of the present disclosure for only one of the walls of the hydration device to include an extension or for neither of the walls to include an extension.

Figure 22:
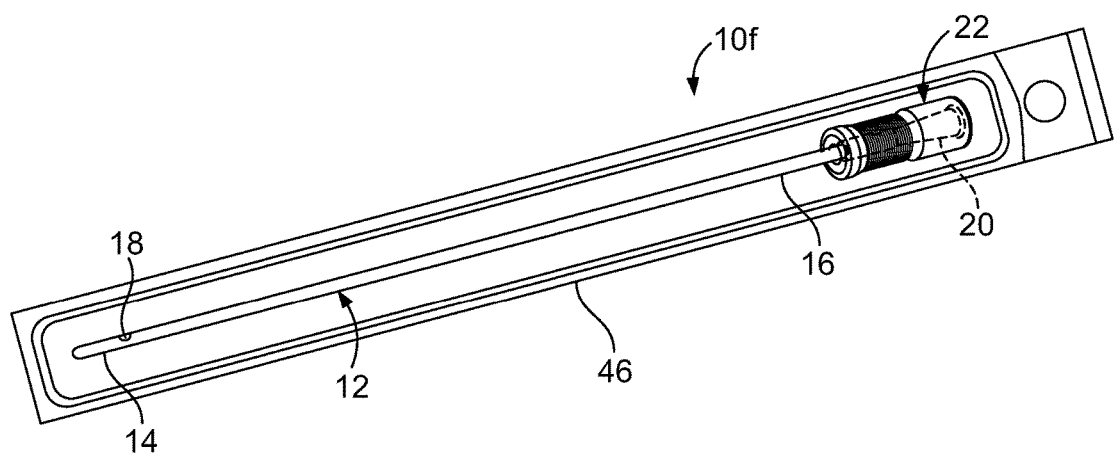
FIG. 22 is a perspective view of an intermittent catheter incorporating a package.
Figure 23:
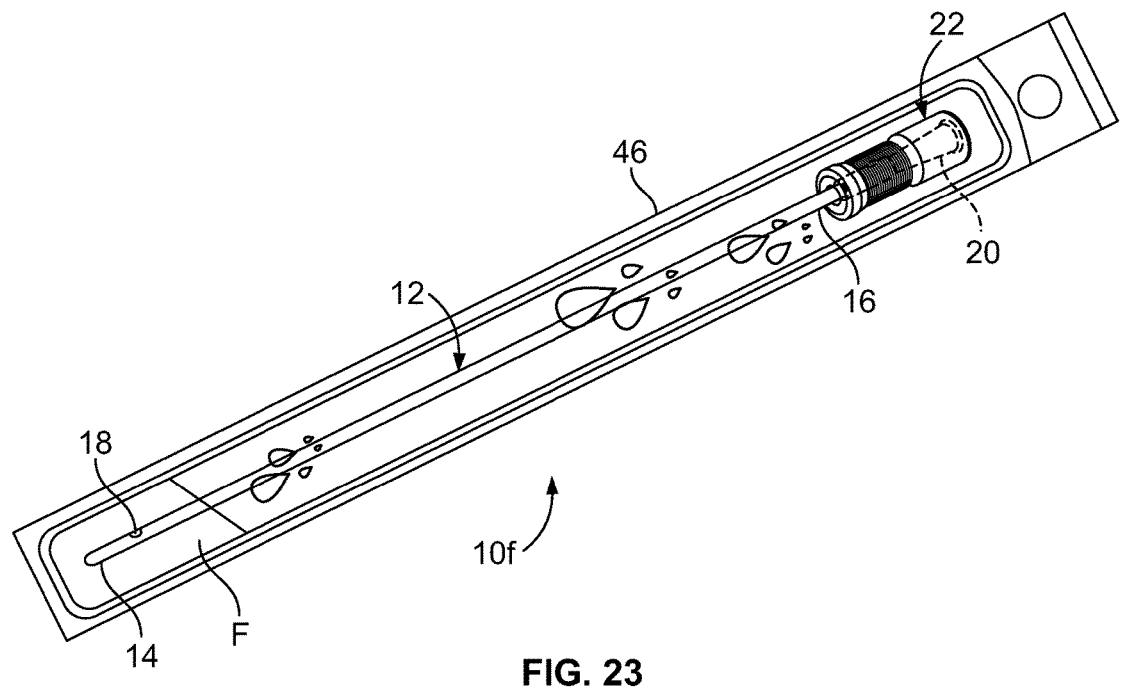
FIG. 23 is a perspective view of the intermittent catheter of FIG. 22, with a hydration device of the intermittent catheter releasing hydrating fluid into the package to contact a catheter shaft of the intermittent catheter.

In addition to the basic components illustrated in FIGS. 1-21, intermittent catheters according to the present disclosure may be provided with additional components without departing from the scope of the present disclosure. For example, FIGS. 22 and 23 show an intermittent catheter 10f positioned within a sealed package 46. In the embodiment of FIGS. 22 and 23, the hydration device 22 may be manipulated (e.g., by pinching or squeezing or being moved proximally along the catheter shaft 12) to release hydrating fluid F into the sealed package 46 (FIG. 23). The package 46 may be manipulated (e.g., by rotating or shaking it) to agitate the hydrating fluid F within the package 46, thereby better coating the catheter shaft 12 with hydrating fluid F. Thereafter, the package 46 may be opened to remove the intermittent catheter 10f for advancement into a body lumen, as described above.

FIG. 24 illustrates an alternative embodiment of a package 46a that may be preferred for use in combination with an intermittent catheter 10g having a hydration device 22 that is manipulated by proximal movement away from the drainage funnel 20. While the package 46a of FIG. 24 may be preferred for use with a hydration device that is manipulated by proximal relative movement, it is also within the scope of the present disclosure for the illustrated package 46a to be used in combination with a hydration device that is configured to be otherwise manipulated for releasing hydrating fluid.

Compared to the package 46 of FIGS. 22 and 23, the package 46a of FIG. 24 includes an additional seal 48, which may seal the package 46a against the hydration device 22. The package 46a is separated into first and second sections 50 and 52, preferably with the intermittent catheter 10g being fully positioned within the second or lower section 52 of the package 46a.

In use, the first section 50 of the package 46a (which may be an unsealed section) may be manipulated to partially separate or break or open the sealed second section 50, without separating or opening the seal 48 between the package 46a and the hydration device 22. In the illustrated embodiment, the first section 50 of the package 46a includes or defines a formation 54, such as a finger hole, for improved gripping and handling of the package 46a by a user when manipulating the first section 50. Preferably, the sealed second section 50 is only separated to the extent necessary to access the distal end of the drainage funnel 20, as shown in FIG. 25. When the second section 50 has only been separated to this limited extent, the seal 48 between the hydration device 22 and the package 46a remains intact, thereby retaining a fluid-tight interface therebetween. FIG. 26 shows the seal 48 being present between the distal end or portion of the hydrating device 22 and the package 46a to provide a fluid-tight interface, but it is within the scope of the present disclosure for the seal 48 be between the package 46a and other surfaces of the hydrating device 22.

Figure 27:
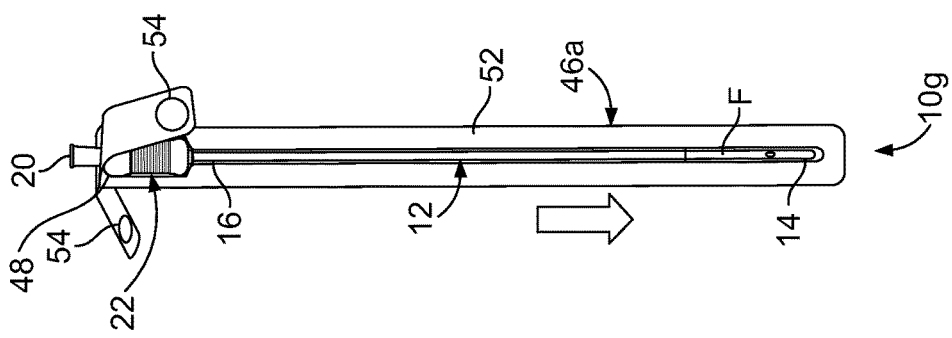

With the second section 50 partially opened, the hydration device 22 may be manipulated to release hydrating fluid F into the second section 52 of the package 46a. FIGS. 26 and 27 show the drainage funnel 20 being moved distally with respect to the hydration device 22 to release hydrating fluid F, but it is within the scope of the present disclosure for the hydration device 22 to be otherwise manipulated to release hydrating fluid F.

Figure 29:
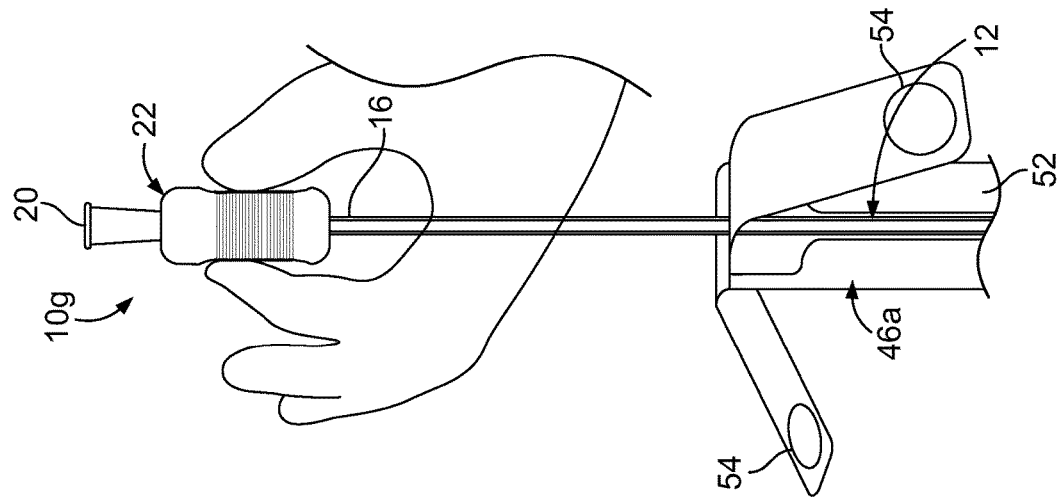
FIG. 29 is a perspective view of the intermittent catheter of FIG. 24, with the intermittent catheter being removed from the package for use.
Figure 28:
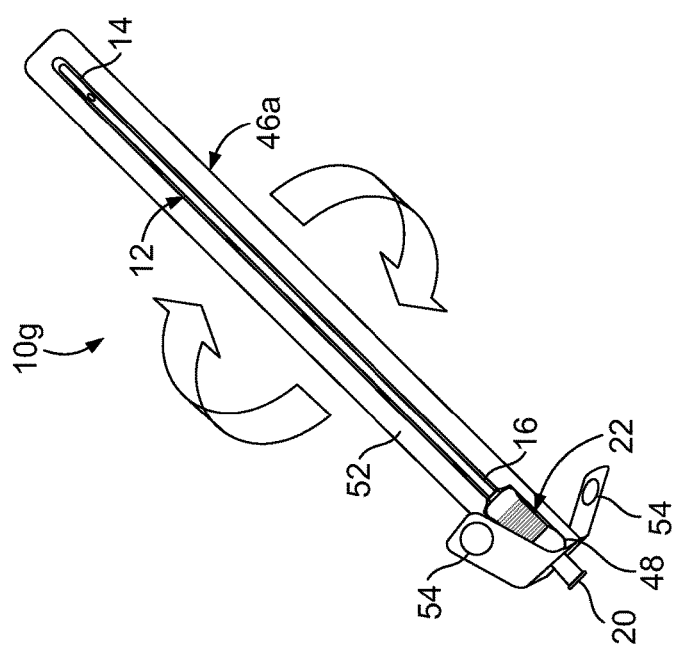
FIG. 28 is a perspective view of the intermittent catheter of FIG. 24, with the package being manipulated to apply hydrating fluid to the catheter shaft.

With hydrating fluid F in the second section 52 of the package 46a, the package 46a may be manipulated (e.g., by rotating or shaking it) to agitate the hydrating fluid F within the second section 52, thereby better coating the catheter shaft 12 with hydrating fluid F. As the fluid-tight seal 48 between the package 46a and the hydration device 22 remains intact, hydrating fluid F is prevented from leaking out of the second section 52 between the hydration device 22 and the seal 48, even when the package 46a is inverted (FIG. 28). Thereafter, the seal 48 may be peeled apart or broken or opened to separate the package 46a from the hydration device 22, allowing the hydration device 22 and the intermittent catheter 10g to be removed (FIG. 29) for advancement into a body lumen, as described above.

FIGS. 30 and 31 illustrate an embodiment of an intermittent catheter 10h having a protective sleeve 56 surrounding at least a portion of the catheter shaft 12 to separate the enclosed portion of the catheter shaft 12 from the outside environment. The protective sleeve 56 may be sealed to the hydration device 22 at or adjacent to a distal portion of the sleeve 56 and sealed about the catheter shaft 12 at or adjacent to a proximal portion of the sleeve 56. Prior to advancement of the catheter shaft 12 into a body lumen, the hydration device 22 may be manipulated (as described above) to release hydrating fluid F into the sleeve 56, as shown in FIG. 31, to lubricate the portion of the catheter shaft 12 positioned within the sleeve 56. Thereafter, the catheter shaft 12 may be moved proximally with respect to the sleeve 56 (while handling the catheter shaft 12 with the sleeve 56) to advance the lubricated catheter shaft 12 into a body lumen. In the embodiment of FIGS. 30 and 31, it may be preferred for the hydration device 22 to remain secured to the drainage funnel 20 during use, but it is also within the scope of the present disclosure for the hydration device 22 to be moved off of the drainage funnel 20 during use.

Figure 32:
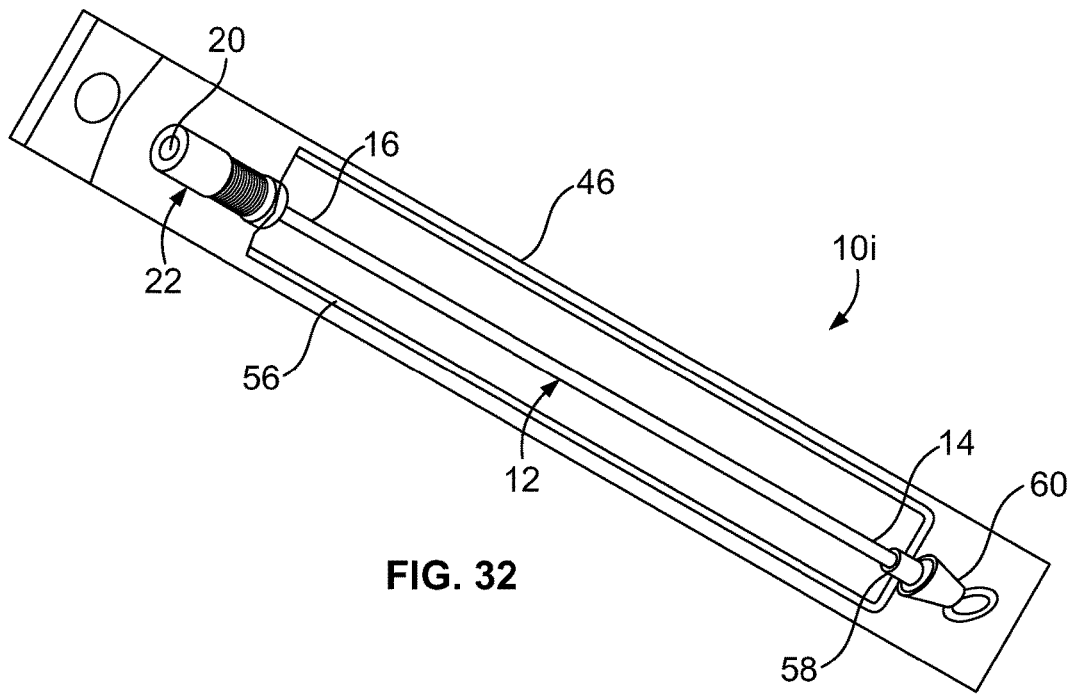
FIG. 32 is a perspective view of an embodiment of an intermittent catheter having a sleeve secured to a hydration device and an introducer tip, positioned within a package.
Figure 33:
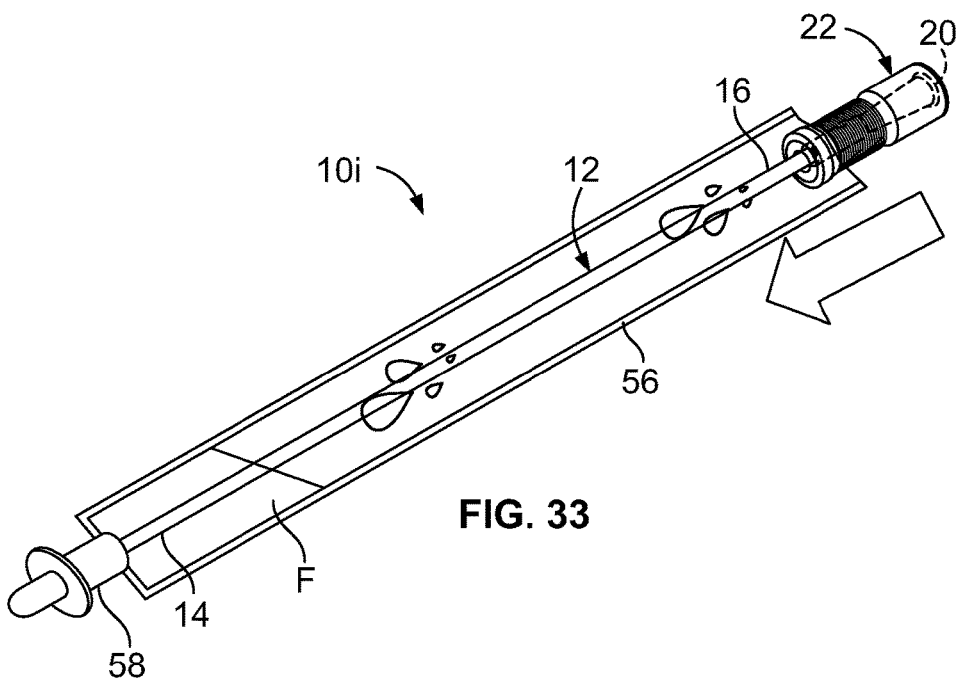
FIG. 33 is a perspective view of the intermittent catheter of FIG. 32, removed from the package for use.

FIGS. 32 and 33 illustrate an embodiment of an intermittent catheter 10i having a protective sleeve 56 and an introducer tip 58. The intermittent catheter 12 may be initially positioned within a package 46 of the type described herein or according to any other suitable design. The introducer tip 58 may be initially positioned within a protective cap 60 that encircles and covers a proximal section of the introducer tip 58. The introducer tip 58 may be provided according to conventional design, associated with the proximal end portion 14 of the catheter shaft 12 and having a proximal section which is advanced into the body lumen prior to proximally advancing the catheter shaft 12 out of the introducer tip 58 and into the body lumen. The protective sleeve 56 may be sealed to the hydration device 22 at or adjacent to a distal portion of the sleeve 56 and sealed to a distal section of the introducer tip 58 at or adjacent to a proximal portion of the sleeve 56.

Prior to advancement of the introducer tip 58 and the catheter shaft 12 into a body lumen, the hydration device 22 may be manipulated (as described above) to release hydrating fluid F into the sleeve 56, as shown in FIG. 33, to wet or lubricate the portion of the catheter shaft 12 positioned within the sleeve 56. Thereafter, the cap 60 may be removed from the introducer tip 58 and then the proximal section of the introducer tip 58 may be positioned within a body lumen. With the introducer tip 58 partially positioned within the body lumen, the catheter shaft 12 may be moved proximally with respect to the introducer tip 58 to advance the wetted or lubricated catheter shaft 12 out of the introducer tip 58 and into the body lumen. In the embodiment of FIGS. 32 and 33, it may be preferred for the hydration device 22 to remain secured to the drainage funnel 20 during use, but it is also within the scope of the present disclosure for the hydration device 22 to be moved off of the drainage funnel 20 during use.

FIGS. 34 and 35 illustrate another embodiment of an intermittent catheter 10j having a protective sleeve 56 and an introducer tip 58. The intermittent catheter 10j of FIGS. 34 and 35 may be configured and used according to the foregoing description of the embodiment of FIGS. 32 and 33, but with the inclusion of a second protective sleeve 62. The second sleeve 62, which is secured at one end to the drainage funnel 20 and at another end to the hydration device 22 in the illustrated embodiment, may be substantially identical to the first sleeve 56 or may be differently configured. By providing a second sleeve 62, the hydration device 22 may be moved proximally along the catheter shaft 12 (e.g., when being used as a gripper device) without uncovering the portion of the catheter shaft 12 that is distal of the hydration device 22. Additionally, if the hydration device 22 is of the type that is manipulated by squeezing to release hydrating fluid, the user may regulate the amount of hydrating fluid F applied to the catheter shaft 12 by squeezing the hydration device 22 while advancing the hydration device 22 along the catheter shaft 12. This may be especially preferred when the fluid is a lubricating fluid, such as an oil or gel.

FIG. 36 illustrates an embodiment of an intermittent catheter 10k having an alternative package 64. In the embodiment of FIG. 36, the intermittent catheter 10k includes a catheter shaft 12 extending between a drainage funnel 20 at its distal end portion 16 and an introducer tip 66 at its proximal end portion. The drainage funnel 20 preferably includes an associated hydration device 22 of the type described herein.

The introducer tip 66 of the intermittent catheter 10k of FIG. 36 may be provided according to conventional design, but preferably is configured as shown in FIGS. 37 and 38. The introducer tip 66 of FIGS. 37 and 38 includes a proximal section 68 configured to be advanced into a body lumen. The proximal section 68 may include a proximal end 70 that is configured to move from a closed condition to an open condition for proximal passage of the catheter shaft 12 therethrough. For example, in the illustrated embodiment the proximal end 70 of the introducer tip 66 is defined by a plurality of flaps or petals that close the hollow proximal section 68 of the introducer tip 66 in the illustrated closed condition, but are sufficiently flexed to be pressed outwardly as the catheter shaft 12 is advanced proximally with respect to the introducer tip 66 to open the proximal end 70 for advancement of the catheter shaft 12 out of the introducer tip 66 and into a body lumen.

The introducer tip 66 also includes a distal section 72 having a greater diameter than the proximal section 68. The illustrated distal section 72 includes a barrel portion 74 and a rim portion 76. The illustrated barrel section 74 is generally tubular or annular and substantially coaxial with the proximal section 68 of the introducer tip 66. The barrel portion 74 is configured to have a greater diameter than the body lumen into which the proximal section 68 is to be advanced. By such a configuration, the barrel portion 74 abuts the body when the introducer tip 66 has been sufficiently advanced into the body lumen, thereby preventing over-insertion of the introducer tip 66 into the body lumen. As for the rim portion 76, it may be generally tubular or annular and surround or encircle the barrel portion 74. The illustrated rim portion 76 is in contact with the barrel portion 74 in at least one location and spaced away from the barrel portion 74 in at least one location so as to define at least one opening 78 between the barrel portion 74 and the rim portion 76. In a preferred embodiment, the rim portion 76 contacts the barrel portion 74 at two locations and spaced away from the barrel portion 74 at two locations to define two openings 78 between the barrel portion 74 and the rim portion 76. In the illustrated embodiment, the barrel portion 74 is substantially symmetrical and defines two diametrically opposed, mirror-image openings 78, but it is also within the scope of the present disclosure for the barrel and rim portions to define more than two openings and/or differently shaped openings and/or openings that are differently arranged around the barrel portion. The introducer tip 66 of FIGS. 37 and 38 may be advantageous in that its openings 78 allow for hydrating fluid released from the hydration device 22 to flow proximally along the catheter shaft 12 and then through the openings 78 to contact and lubricate the proximal section 68 of the introducer tip 66.

The catheter shaft 12, drainage funnel 20, hydration device 22, and introducer tip 66 are positioned within a sleeve package 64, as shown in FIG. 36. The sleeve package 64 is similar to the package 46a of FIG. 24, but includes an additional seal, which defines a third section. In particular, the sleeve package 64 includes proximal and distal end seals 80 and 82 at or adjacent to its ends. Two opposing surfaces or sheets of the sleeve package 64 are sealed together to seal the interior of the sleeve package 64 from the outside environment. The sleeve package 64 further includes proximal and distal intermediate seals 84 and 86, with the proximal intermediate seal 84 being between the sleeve package 64 and the rim portion 76 of the introducer tip 66, and the distal intermediate seal 86 being between the sleeve package 64 and the hydration device 22. A sealed proximal chamber 88 is defined between the proximal end seal 80 and the proximal intermediate seal 84 and receives a portion of the introducer tip 66 (namely, the proximal section 68 of the introducer tip 66). A sealed distal chamber 90 is defined between the distal end seal 82 and the distal intermediate seal 86 and receives a portion of the drainage funnel 20. A sealed intermediate chamber 92 is defined between the proximal intermediate seal 84 and the distal intermediate seal 86 and receives a portion of the catheter shaft 12.

In use, the distal end seal 82 may be opened by a user (e.g., by tearing it or peeling it apart) to open the sealed distal chamber 90, thereby allowing direct access to the drainage funnel 20 and/or a portion of the hydration device 22 (FIG. 39). With the sealed distal chamber 90 opened, the user may manipulate the hydration device 22 to release hydrating fluid F into the sealed intermediate chamber 92, where it contacts and coats the catheter shaft 12. The hydrating fluid flows proximally along the catheter shaft 12 and through the openings 78 of the introducer tip 66 into the sealed proximal chamber 88, where the hydrating fluid lubricates the proximal section 68 of the introducer tip 66. The hydrating fluid may be a lubricant itself or a fluid that interacts with a coating of the introducer tip 66 (e.g., a hydrophilic coating) to lubricate the introducer tip 66. Alternatively, rather than opening the sealed distal section 90 prior to releasing the hydrating fluid, it is also within the scope of the present disclosure for the hydrating fluid to be released prior to opening the sealed distal section 90.

When the catheter shaft 12 and/or the proximal section 68 of the introducer tip 66 have been lubricated, the user may open the proximal end seal 80 (e.g., by tearing it or peeling it apart) to open the sealed proximal chamber 88. The intermediate seals 84 and 86 remain intact, thereby maintaining the integrity of the sealed intermediate section 92 of the sleeve package 64, which acts as a protective sleeve during use of the intermittent catheter 10k.

With both the sealed proximal chamber 88 and the sealed distal chamber 90 opened, the introducer tip 66 may be advanced into the body lumen up to the point that the barrel portion 74 of the distal section 72 contacts the body. At that point, the catheter shaft 12 may be advanced proximally with respect to the introducer tip 66 (e.g., by gripping the hydration device 22 and moving it and the catheter shaft 12 toward the body lumen) to advance the catheter shaft 12 proximally out of the introducer tip 66 and into the body lumen, as described above.

Aspects of the present subject matter described above may be beneficial alone or in combination with one or more other aspects. Without limiting the foregoing description, in accordance with one aspect of the subject matter herein, there is provided an intermittent catheter, which includes a catheter shaft extending between a proximal end portion and a distal end portion. A drainage member is associated with the distal end portion of the catheter shaft, while a hydration device encircles at least a portion of the drainage member. The drainage member defines a hydrating fluid-containing reservoir in fluid communication with at least one fluid-release port, with the hydration device being configured to be manipulated by a user to move the at least one fluid-release port from a closed condition to an open condition to flow at least a portion of the hydrating fluid out of the reservoir via the at least one fluid-release port for covering at least a portion of the catheter shaft.

In accordance with another aspect which may be used or combined with the preceding aspect, the hydration device defines a central cavity and at least one fluid-release port is in fluid communication with the central cavity.

In accordance with another aspect which may be used or combined with the preceding aspect, the hydration device is configured to be squeezed by a user to move the at least one fluid-release port from the closed condition to the open condition.

In accordance with another aspect which may be used or combined with the second aspect, the hydration device is configured to be moved proximally along the catheter shaft to move the at least one fluid-release port from the closed condition to the open condition.

In accordance with another aspect which may be used or combined with the first aspect, the hydration device defines a central cavity and the at least one fluid-release port is spaced away from the central cavity.

In accordance with another aspect which may be used or combined with the preceding aspect, the hydration device is configured to be squeezed by a user to move the at least one fluid-release port from the closed condition to the open condition.

In accordance with another aspect which may be used or combined with the preceding aspect, the hydration device includes a plurality of fluid-release ports and is configured to be squeezed by a user in one plane to move at least one of the fluid-release ports from the closed condition to the open condition and in a different plane to move a different one of the fluid-release ports from the closed condition to the open condition.

In accordance with another aspect which may be used or combined with any of the preceding aspects, a package is provided, with the catheter shaft, the drainage member, and the hydration device being received within the package. The hydration device is configured to be manipulated by a user to move the at least one fluid-release port from a closed condition to an open condition to flow at least a portion of the hydrating fluid out of the reservoir via the at least one fluid-release port into the package for covering at least a portion of the catheter shaft.

In accordance with another aspect which may be used or combined with the preceding aspect, the at least one fluid-release port is configured to be moved from the closed condition to the open condition prior to opening the package.

In accordance with another aspect which may be used or combined with the eighth aspect, the package includes first and second sections, with the first section of the package being configured to be manipulated to partially open the second section prior to moving the at least one fluid-release port from the closed condition to the open condition and the second section of the package being configured to be more fully opened after moving the at least one fluid-release port from the closed condition to the open condition.

In accordance with another aspect which may be used or combined with the preceding aspect, a fluid-tight interface is defined between the package and the hydration device in the second section.

In accordance with another aspect which may be used or combined with the preceding aspect, the second section is configured to be partially opened to expose a portion of the drainage member while maintaining the fluid-tight interface between the package and the hydration device.

In accordance with another aspect which may be used or combined with any of the preceding aspects, the reservoir is defined between inner and outer walls of the hydration device, the outer wall including a gripping portion that is sufficiently flexible to be moved toward and into engagement with the inner wall.

In accordance with another aspect which may be used or combined with the preceding aspect, an extension is associated with the gripping portion of the outer wall and positioned within the reservoir. The extension extends toward and is spaced away from the inner wall, with the extension being configured to engage the inner wall when the gripping portion of the outer wall is moved toward the inner wall.

In accordance with another aspect which may be used or combined with any of the preceding two aspects, an outer surface of the gripping portion of the outer wall of the hydration device has a smaller diameter than an outer surface of the outer wall adjacent to the gripping portion.

In accordance with another aspect which may be used or combined with any of the preceding three aspects, at least a portion of an outer surface of the gripping portion of the outer wall of the hydration device is textured for engagement with a digit of a user.

In accordance with another aspect which may be used or combined with any of the preceding four aspects, the inner wall of the hydration device is sufficiently flexible such that movement of the outer wall into engagement with the inner wall moves at least a portion of the inner wall into engagement with the catheter shaft.

In accordance with another aspect which may be used or combined with the preceding aspect, a radially inwardly extending extension is associated with the inner wall of the hydration device. The extension of the inner wall is generally aligned with the gripping portion of the outer wall and is configured to be moved into engagement with the catheter shaft when the outer wall of the hydration device is moved into engagement with the inner wall.

In accordance with another aspect which may be used or combined with any of the preceding aspects, a sleeve is secured to the hydration device and encircles at least a portion of the catheter shaft.

In accordance with another aspect which may be used or combined with the preceding aspect, an introducer tip is associated with the proximal end portion of the catheter shaft and is secured to the sleeve.

In accordance with another aspect which may be used or combined with any of the preceding two aspects, a second sleeve is secured at one end to the hydration device and at another end to the drainage member.

In accordance with another aspect which may be used or combined with any of the preceding aspects, the catheter shaft includes a hydrophilic outer surface along at least a portion of the catheter shaft and the hydrating fluid is configured to contact and wet at least a portion of the hydrophilic outer surface of the catheter shaft.

In accordance with another aspect which may be used or combined with any of the first twenty-one aspects, the hydrating fluid is configured to contact and lubricate a non-hydrophilic portion of an outer surface of the catheter shaft.

In accordance with another aspect, there is provided an intermittent catheter, which includes a catheter shaft extending between a proximal end portion and a distal end portion. An introducer tip is associated with the proximal end portion of the catheter shaft and has proximal and distal sections. The distal section has a barrel portion and a rim portion, with the rim portion surrounding the barrel portion and being in contact with the barrel portion in at least one location and spaced away from the barrel portion in at least one location to define at least one opening between the barrel and rim portions.

In accordance with another aspect which may be used or combined with the preceding aspect, the rim portion is in contact with the barrel portion at two locations and is spaced away from the barrel portion at two locations to define two openings between the barrel and rim portions.

In accordance with another aspect which may be used or combined with any of the preceding two aspects, a drainage member is associated with the distal end portion of the catheter shaft. A hydration device encircles at least a portion of the drainage member, defining a hydrating fluid-containing reservoir. The hydration device is configured to be manipulated by a user to flow at least a portion of the hydrating fluid out of the reservoir for covering at least a portion of the catheter shaft. A sleeve package is secured to the rim portion of the introducer tip and to the hydration device to define a sleeve portion therebetween. The sleeve package includes a sealed proximal chamber receiving a portion of the introducer tip and a sealed distal chamber receiving a portion of the drainage member.

In accordance with another aspect which may be used or combined with the preceding aspect, the sealed proximal and distal chambers are configured to be open during use of the intermittent catheter, with the sleeve package remaining secured to the rim portion of the introducer tip and to the hydration device during use.

In accordance with another aspect, there is provided a method of hydrating an intermittent catheter. The method includes providing an intermittent catheter including a catheter shaft extending between a proximal end portion and a distal end portion, a drainage member associated with the distal end portion of the catheter shaft, and a hydration device encircling at least a portion of the drainage member and defining a hydrating fluid-containing reservoir in fluid communication with at least one fluid-release port. The hydration device is manipulated to move the at least one fluid-release port from a closed condition to an open condition to flow at least a portion of the hydrating fluid out of the reservoir via the at least one fluid-release port, thereby covering at least a portion of the catheter shaft with the hydrating fluid.

In accordance with another aspect which may be used or combined with the preceding aspect, manipulating the hydration device includes flowing at least a portion of the hydrating fluid out of the reservoir via a fluid-release port in fluid communication with a central cavity defined by the hydration device.

In accordance with another aspect which may be used or combined with any of the preceding two aspects, manipulating the hydration device includes squeezing the hydration device.

In accordance with another aspect which may be used or combined with either of the twenty-eighth and twenty-ninth aspects, manipulating the hydration device includes moving the hydration device proximally along the catheter shaft.

In accordance with another aspect which may be used or combined with the twenty-eighth aspect, manipulating the hydration device includes flowing at least a portion of the hydrating fluid out of the reservoir via a fluid-release port that is spaced away from a central cavity defined by the hydration device.

In accordance with another aspect which may be used or combined with the preceding aspect, manipulating the hydration device includes squeezing the hydration device.

In accordance with another aspect which may be used or combined with the preceding aspect, at least one of the fluid-release ports remains in the closed condition upon squeezing the hydration device.

In accordance with another aspect which may be used or combined with any of the preceding seventh aspects, providing an intermittent catheter includes providing an intermittent catheter received within a package. Manipulating the hydration device includes flowing at least a portion of the hydrating fluid into the package for covering at least a portion of the catheter shaft.

In accordance with another aspect which may be used or combined with the preceding aspect, the method includes opening the package after covering at least a portion of the catheter shaft with the hydrating fluid.

In accordance with another aspect which may be used or combined with the thirty-fifth aspect, the package includes first and second sections. The method includes opening the first section of the package prior to manipulating the hydration device and opening the second section of the package after covering at least a portion of the catheter shaft with the hydrating fluid.

In accordance with another aspect which may be used or combined with any of the preceding ten aspects, the reservoir is defined between inner and outer walls of the hydration device. The method includes moving a gripping portion of the outer wall into engagement with the inner wall after covering at least a portion of the catheter shaft with the hydrating fluid.

In accordance with another aspect which may be used or combined with the preceding aspect, the gripping portion of the outer wall of the hydration device includes an extension positioned within the reservoir. Moving the gripping portion of the outer wall into engagement with the inner wall includes moving the extension of the gripping portion into engagement with the inner wall.

In accordance with another aspect which may be used or combined with any of the preceding two aspects, moving the gripping portion of the outer wall into engagement with the inner wall includes moving at least a portion of the inner wall into engagement with the catheter shaft.

In accordance with another aspect which may be used or combined with the preceding aspect, the inner wall includes a radially inwardly extending extension generally aligned with the gripping portion of the outer wall. Moving at least a portion of the inner wall into engagement with the catheter shaft includes moving the extension of the inner wall into engagement with the catheter shaft.

In accordance with another aspect which may be used or combined with any of the preceding fourteen aspects, providing an intermittent catheter includes providing a sleeve secured to the hydration device and encircling at least a portion of the catheter shaft, while manipulating the hydration device includes flowing at least a portion of the hydrating fluid into the sleeve for covering at least a portion of the catheter shaft.

In accordance with another aspect which may be used or combined with the preceding aspect, providing an intermittent catheter includes providing a second sleeve secured at one end to the hydration device and at another end to the drainage member.

In accordance with another aspect which may be used or combined with any of the preceding sixteen aspects, the catheter shaft includes a hydrophilic outer surface along at least a portion of the catheter shaft and the hydrating fluid covers and wets at least a portion of the hydrophilic outer surface of the catheter shaft.

In accordance with another aspect which may be used or combined with any of the twenty-eighth through forty-third aspects, the hydrating fluid covers and lubricates a non-hydrophilic portion of an outer surface of the catheter shaft.

In accordance with another aspect, there is provided a method of hydrating an intermittent catheter. The method includes providing an intermittent catheter including a catheter shaft extending between a proximal end portion and a distal end portion and an introducer tip associated with the proximal end portion. A hydrating fluid is applied to the catheter shaft and the introducer tip, with the hydrating fluid first being applied to a portion of the catheter shaft positioned distally of the introducer tip, then the hydrating fluid flowing proximally along the catheter shaft to contact a distal section of the introducer tip, and then the hydrating fluid flowing proximally through at least one opening defined by the distal section of the introducer tip to contact a proximal section of the introducer tip.

In accordance with another aspect which may be used or combined with the preceding aspect, providing an intermittent catheter includes providing an intermittent catheter received within a package, while applying a hydrating fluid to the catheter shaft and the introducer tip includes flowing the hydrating fluid into the package.

In accordance with another aspect which may be used or combined with any of the preceding two aspects, the intermittent catheter includes a drainage member associated with the distal end portion of the catheter shaft, a hydrating fluid-containing hydration device encircling at least a portion of the drainage member, and a sleeve package secured to the introducer tip and the hydration device to define a sleeve portion therebetween. The sleeve package includes a sealed proximal chamber receiving a portion of the introducer tip and a sealed distal chamber receiving a portion of the drainage member. Applying a hydrating fluid to the catheter shaft and the introducer tip includes flowing said hydrating fluid out of the hydration device and into the sleeve portion, and further comprising opening the proximal and distal chambers of the sleeve package after applying hydrating fluid to the catheter shaft and the introducer tip while the sleeve package remains secured to the introducer tip and to the hydration device.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. An intermittent catheter comprising:
   a catheter shaft extending between a proximal end portion and a distal end portion;
   a drainage member associated with the distal end portion of the catheter shaft;
   a hydration device encircling at least a portion of the drainage member and defining a hydrating fluid-containing reservoir in fluid communication with at least one fluid-release port; and
   a package or sleeve in which the catheter shaft and the hydration device are at least partially positioned, wherein the hydration device is configured to be manipulated while at least partially positioned within the package or sleeve by a user to move the at least one fluid-release port from a closed condition to an open condition to flow at least a portion of the hydrating fluid out of the reservoir and into the package or sleeve via the at least one fluid-release port for covering at least a portion of the catheter shaft.

2. The intermittent catheter of claim 1, wherein the hydration device defines a central cavity and the at least one fluid-release port is in fluid communication with the central cavity.

3. The intermittent catheter of claim 2, wherein the hydration device is configured to be squeezed by a user to move the at least one fluid-release port from the closed condition to the open condition.

4. The intermittent catheter of claim 2, wherein the hydration device is configured to be moved proximally along the catheter shaft to move the at least one fluid-release port from the closed condition to the open condition.

5. The intermittent catheter of claim 1, wherein the hydration device defines a central cavity and the at least one fluid-release port is spaced away from the central cavity.

6. The intermittent catheter of claim 5, wherein the hydration device is configured to be squeezed by a user to move the at least one fluid-release port from the closed condition to the open condition.

7. The intermittent catheter of claim 6, wherein the hydration device includes a plurality of fluid-release ports and is configured to be squeezed by a user in one plane to move at least one of the fluid-release ports from the closed condition to the open condition and in a different plane to move a different one of the fluid-release ports from the closed condition to the open condition.

8. The intermittent catheter of claim 1, wherein the package includes first and second sections, with the first section of the package being configured to be manipulated to partially open the second section prior to moving the at least one fluid-release port from the closed condition to the open condition and the second section of the package being configured to be more fully opened after moving the at least one fluid-release port from the closed condition to the open condition.

9. The intermittent catheter of claim 1, wherein said package or sleeve comprises a sleeve secured to the hydration device and encircling at least a portion of the catheter shaft.

10. The intermittent catheter of claim 9, further comprising an introducer tip associated with the proximal end portion of the catheter shaft and secured to the sleeve.

11. The intermittent catheter of claim 9, further comprising a second sleeve secured at one end to the hydration device and at another end to the drainage member.

12. An intermittent catheter comprising:
    a catheter shaft extending between a proximal end portion and a distal end portion;
    a drainage member associated with the distal end portion of the catheter shaft; and
    a hydration device encircling at least a portion of the drainage member and defining a hydrating fluid-containing reservoir in fluid communication with at least one fluid-release port, wherein
    the hydration device is configured to be manipulated by a user to move the at least one fluid-release port from a closed condition to an open condition to flow at least a portion of the hydrating fluid out of the reservoir via the at least one fluid-release port for covering at least a portion of the catheter shaft, and
    the reservoir is defined between inner and outer walls of the hydration device, the outer wall including a gripping portion that is sufficiently flexible to be moved toward and into engagement with the inner wall.

13. The intermittent catheter of claim 12, further comprising an extension associated with the gripping portion of the outer wall and positioned within the reservoir, the extension extending toward and spaced away from the inner wall, wherein the extension is configured to engage the inner wall when the gripping portion of the outer wall is moved toward the inner wall.

14. The intermittent catheter of claim 12, wherein the inner wall of the hydration device is sufficiently flexible such that movement of the outer wall into engagement with the inner wall moves at least a portion of the inner wall into engagement with the catheter shaft.

15. The intermittent catheter of claim 14, further comprising a radially inwardly extending extension associated with the inner wall of the hydration device, wherein the extension of the inner wall is generally aligned with the gripping portion of the outer wall and configured to be moved into engagement with the catheter shaft when the outer wall of the hydration device is moved into engagement with the inner wall.

16. An intermittent catheter comprising:
    a catheter shaft extending between a proximal end portion and a distal end portion; and
    an introducer tip associated with the proximal end portion of the catheter shaft and comprising proximal and distal sections, wherein the distal section comprises a barrel portion receiving a portion of the catheter shaft, and a rim portion, with the rim portion surrounding the barrel portion and being in contact with the barrel portion in at least one location and spaced away from the barrel portion in at least one location to define at least one opening between the barrel and rim portions and configured to allow fluid flow through the rim portion between positions proximal and distal of the rim portion.

17. The intermittent catheter of claim 16, further comprising a hydration device encircling at least a portion of the catheter shaft, and a sleeve package receiving at least a portion of the catheter shaft and including proximal and distal end seals between opposing surfaces of the sleeve package, a proximal intermediate seal between the sleeve package and the rim portion of the introducer tip, and a distal intermediate seal between the sleeve package and the hydration device.

18. A method of hydrating an intermittent catheter comprising:

providing an intermittent catheter including a catheter shaft extending between a proximal end portion and a distal end portion, a drainage member associated with the distal end portion of the catheter shaft, a hydration device encircling at least a portion of the drainage member and defining a hydrating fluid-containing reservoir in fluid communication with at least one fluid-release port, and a package or sleeve in which the catheter shaft and the hydration device are at least partially positioned; and manipulating the hydration device while at least partially positioned within the package or sleeve to move the at least one fluid-release port from a closed condition to an open condition to flow at least a portion of the hydrating fluid out of the reservoir and into the package or sleeve via the at least one fluid-release port, thereby covering at least a portion of the catheter shaft with the hydrating fluid.

19. The method of claim 18, wherein said manipulating the hydration device includes squeezing the hydration device.

20. The method of claim 18, wherein said manipulating the hydration device includes moving the hydration device proximally along the catheter shaft.

* * * * *